US012697467B2

(12) United States Patent
Yin et al.

(10) Patent No.: US 12,697,467 B2
(45) Date of Patent: *Aug. 4, 2026

(54) URINARY CATHETER

(71) Applicant: C. R. Bard, Inc., Franklin Lakes, NJ (US)

(72) Inventors: Zhihui Yin, Lilburn, GA (US); David Fish, Rutledge, GA (US); Tom Roberts, Bishop, GA (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 181 days.

This patent is subject to a terminal disclaimer.

(21) Appl. No.: 18/536,063

(22) Filed: Dec. 11, 2023

(65) Prior Publication Data

US 2024/0108850 A1 Apr. 4, 2024

Related U.S. Application Data

(63) Continuation of application No. 17/114,275, filed on Dec. 7, 2020, now Pat. No. 11,850,370, which is a
(Continued)

(51) Int. Cl.
*A61M 25/00* (2006.01)
*A61L 29/08* (2006.01)
(Continued)

(52) U.S. Cl.
CPC ....... *A61M 25/0017* (2013.01); *A61L 29/085* (2013.01); *A61L 29/14* (2013.01);
(Continued)

(58) Field of Classification Search
CPC ...... A61M 25/0017; A61M 2025/0046; A61M 25/0045; A61M 2025/0056;
(Continued)

(56) References Cited

U.S. PATENT DOCUMENTS

| | | | |
|---|---|---|---|
| 426,931 | A | 4/1890 | Flower |
| 734,498 | A | 7/1903 | Bachler |

(Continued)

FOREIGN PATENT DOCUMENTS

| | | |
|---|---|---|
| AU | 2016283336 A1 | 12/2017 |
| AU | 2014362360 B2 | 1/2020 |

(Continued)

OTHER PUBLICATIONS

"Medifilm." Datasheet [online]. Mylan Technologies Inc., 2003 [retrieved on Feb. 14, 2020]. Retrieved from the Internet: <URL: https://web.archive.org/web/20030205090818/http://www.mylantech. com/products/medifilm.html>.

(Continued)

*Primary Examiner* — Adam Marcetich
(74) *Attorney, Agent, or Firm* — Rutan & Tucker LLP

(57) ABSTRACT

A urinary catheter and container. The urinary catheter can include a catheter shaft attached to a handle and a coating disposed on an outer surface of the catheter shaft. The coating can include a hydrogel, water and/or glycerin, and a polyethylene gylcol (PEG). The PEG can have a molecular weight equal to or less than 600, for example one or more of polyethylene glycol (PEG) 300 and PEG 400. The coating can be applied in a wet state and remain wet for an extended period of time in the container, thereby obviating the need for a lubricant, such as a water sachet or gel package, to accompany the catheter in the container. The container can include a gas impermeable foil material. The container can include an adhesive tab covering a perforated section, the adhesive tab including a pull loop.

20 Claims, 7 Drawing Sheets

Related U.S. Application Data continuation of application No. 15/506,723, filed as application No. PCT/US2015/047026 on Aug. 26, 2015, now Pat. No. 10,857,324.

(60) Provisional application No. 62/042,125, filed on Aug. 26, 2014.

(51) Int. Cl.
   *A61L 29/14*      (2006.01)
   *A61M 25/01*      (2006.01)

(52) U.S. Cl.
   CPC ......... *A61L 29/145* (2013.01); *A61M 25/002* (2013.01); *A61M 25/0045* (2013.01); *A61M 25/007* (2013.01); *A61M 25/0136* (2013.01); *A61L 29/08* (2013.01); *A61L 29/141* (2013.01); *A61L 2400/10* (2013.01); *A61L 2420/08* (2013.01); *A61M 25/0009* (2013.01); *A61M 2025/0046* (2013.01)

(58) Field of Classification Search
   CPC ...... A61M 25/0009; A61M 2210/1089; A61M 25/0014; A61M 25/0021; A61L 29/085; A61L 2420/08; A61L 29/14; A61L 2400/10; A61L 31/10; A61L 2420/02; A61L 2300/404; A61L 29/08; A61L 29/141; A61L 29/145; A61L 2300/606
   See application file for complete search history.

(56) References Cited

U.S. PATENT DOCUMENTS

| | | | |
|---|---|---|---|
| 1,131,865 A | 3/1915 | Putnam et al. | |
| 1,235,142 A | 7/1917 | Ichilian | |
| 1,304,396 A | 5/1919 | Smith | |
| 1,643,289 A | 9/1927 | Emile | |
| 1,661,494 A | 3/1928 | Nielsen | |
| 1,876,229 A | 9/1932 | Oliver et al. | |
| 1,888,349 A | 11/1932 | Jacoby | |
| 1,978,497 A | 10/1934 | Lind | |
| 2,043,630 A | 6/1936 | Raiche | |
| 2,213,210 A | 9/1940 | Egbert | |
| 2,228,992 A | 1/1941 | Fry | |
| 2,230,226 A | 2/1941 | Auzin | |
| 2,248,934 A | 7/1941 | Auzin | |
| 2,262,749 A | 11/1941 | Berwald | |
| 2,285,502 A | 6/1942 | Dreyfus | |
| 2,308,484 A | 1/1943 | Auzin et al. | |
| 2,314,262 A | 3/1943 | Winder | |
| 2,320,157 A | 5/1943 | Raiche | |
| 2,322,858 A | 6/1943 | Limbert et al. | |
| 2,330,399 A | 9/1943 | Winder | |
| 2,330,400 A | 9/1943 | Winder | |
| 2,389,831 A | 11/1945 | Welsh | |
| 2,390,070 A | 12/1945 | Auzin | |
| 2,481,488 A | 9/1949 | Auzin | |
| 2,494,393 A | 1/1950 | Lamson | |
| 2,610,626 A | 9/1952 | Edwards | |
| 2,638,093 A | 5/1953 | Kulick | |
| 2,648,463 A | 8/1953 | Robert | |
| 2,649,619 A | 8/1953 | Killian | |
| 2,649,854 A | 8/1953 | Salm | |
| 2,690,595 A | 10/1954 | Raiche | |
| 2,712,161 A | 7/1955 | Moss | |
| 2,856,932 A | 10/1958 | Griffitts | |
| 2,912,981 A | 11/1959 | Keough | |
| 2,919,697 A | 1/1960 | Kim | |
| 3,035,691 A | 5/1962 | Kai et al. | |
| 3,044,468 A | 7/1962 | Birtwell | |
| 3,053,257 A | 9/1962 | Birtwell | |
| 3,076,464 A | 2/1963 | Rosenberg | |
| 3,169,527 A | 2/1965 | Sheridan | |
| 3,173,566 A | 3/1965 | Talbert | |
| 3,211,151 A | 10/1965 | Foderick et al. | |
| 3,246,075 A | 4/1966 | Dansard | |
| 3,249,285 A | 5/1966 | Franz et al. | |
| 3,304,353 A | 2/1967 | Harautuneian | |
| 3,344,791 A | 10/1967 | Foderick | |
| 3,345,988 A | 10/1967 | Vitello | |
| 3,394,704 A | 7/1968 | Dery | |
| 3,394,705 A | 7/1968 | Abramson | |
| 3,403,682 A | 10/1968 | McDonell | |
| 3,409,016 A | 11/1968 | Foley | |
| 3,434,869 A | 3/1969 | Davidson | |
| 3,463,141 A | 8/1969 | Mozolf | |
| 3,478,743 A | 11/1969 | Ericson | |
| 3,503,400 A | 3/1970 | Osthagen | |
| 3,508,959 A | 4/1970 | Krahnke | |
| 3,509,884 A | 5/1970 | Bell | |
| 3,520,305 A | 7/1970 | Davis | |
| 3,539,674 A | 11/1970 | Dereniuk et al. | |
| 3,544,668 A | 12/1970 | Dereniuk | |
| 3,548,805 A | 12/1970 | Datsenko | |
| 3,556,294 A | 1/1971 | Walck et al. | |
| 3,556,874 A | 1/1971 | McClain | |
| 3,566,874 A | 3/1971 | Shepherd et al. | |
| 3,593,713 A | 7/1971 | Bogoff et al. | |
| 3,598,127 A | 8/1971 | Wepsic | |
| 3,606,889 A | 9/1971 | Arblaster | |
| 3,642,004 A | 2/1972 | Osthagen et al. | |
| 3,646,929 A | 3/1972 | Bonnar | |
| 3,648,704 A | 3/1972 | Jackson | |
| 3,648,891 A | 3/1972 | Katz et al. | |
| 3,651,615 A | 3/1972 | Bohner et al. | |
| 3,683,928 A | 8/1972 | Kuntz | |
| 3,695,921 A | 10/1972 | Shepherd et al. | |
| 3,699,956 A | 10/1972 | Kitrilakis et al. | |
| 3,699,964 A | 10/1972 | Ericson | |
| 3,708,324 A | 1/1973 | Stebleton | |
| 3,726,281 A | 4/1973 | Norton et al. | |
| 3,739,783 A | 6/1973 | Broerman | |
| 3,761,013 A | 9/1973 | Schuster | |
| 3,762,399 A | 10/1973 | Riedell | |
| 3,768,102 A | 10/1973 | Kwan-Gett et al. | |
| 3,788,324 A | 1/1974 | Lim | |
| 3,794,042 A | 2/1974 | De Klotz et al. | |
| 3,797,478 A | 3/1974 | Walsh et al. | |
| 3,802,987 A | 4/1974 | Noll | |
| 3,835,992 A | 9/1974 | Adams, IV | |
| 3,838,728 A | 10/1974 | Voegele | |
| 3,841,304 A | 10/1974 | Jones | |
| 3,854,483 A | 12/1974 | Powers | |
| 3,861,395 A | 1/1975 | Taniguchi | |
| 3,875,937 A | 4/1975 | Schmitt et al. | |
| 3,879,516 A | 4/1975 | Wolvek | |
| 3,882,220 A | 5/1975 | Ryder | |
| 3,889,685 A | 6/1975 | Miller, Jr. et al. | |
| 3,894,540 A | 7/1975 | Bonner, Jr. | |
| 3,898,993 A | 8/1975 | Taniguchi | |
| 3,924,634 A | 12/1975 | Taylor et al. | |
| 3,926,309 A | 12/1975 | Center | |
| 3,926,705 A | 12/1975 | Todd | |
| 3,930,580 A | 1/1976 | Bazell et al. | |
| 3,934,721 A | 1/1976 | Juster et al. | |
| 3,962,519 A | 6/1976 | Rusch et al. | |
| 3,967,728 A | 7/1976 | Gordon et al. | |
| 3,981,299 A | 9/1976 | Murray | |
| 3,983,879 A | 10/1976 | Todd | |
| 4,026,296 A | 5/1977 | Stoy et al. | |
| 4,029,104 A | 6/1977 | Kerber | |
| 4,051,849 A | 10/1977 | Poncy et al. | |
| 4,055,682 A | 10/1977 | Merrill | |
| 4,062,363 A | 12/1977 | Bonner, Jr. | |
| 4,069,359 A | 1/1978 | DeMarse et al. | |
| 4,091,922 A | 5/1978 | Egler | |
| 4,119,094 A | 10/1978 | Micklus et al. | |
| 4,120,715 A | 10/1978 | Ockwell et al. | |
| 4,133,303 A | 1/1979 | Patel | |
| 4,140,127 A | 2/1979 | Cianci et al. | |
| 4,149,539 A | 4/1979 | Cianci | |
| 4,168,699 A | 9/1979 | Hauser | |
| 4,170,996 A | 10/1979 | Wu | |

(56)  References Cited

U.S. PATENT DOCUMENTS

| | | |
|---|---|---|
| 4,186,745 A | 2/1980 | Lewis et al. |
| 4,187,851 A | 2/1980 | Hauser |
| 4,196,731 A | 4/1980 | Laurin et al. |
| 4,198,983 A | 4/1980 | Becker et al. |
| 4,198,984 A | 4/1980 | Taylor |
| 4,209,010 A | 6/1980 | Ward et al. |
| 4,225,371 A | 9/1980 | Taylor et al. |
| 4,230,115 A | 10/1980 | Walz, Jr. et al. |
| 4,245,639 A | 1/1981 | La Rosa |
| 4,246,909 A | 1/1981 | Wu et al. |
| 4,249,535 A | 2/1981 | Hargest, III |
| 4,252,760 A | 2/1981 | Foster et al. |
| 4,265,848 A | 5/1981 | Rusch |
| 4,266,999 A | 5/1981 | Baier |
| 4,269,310 A | 5/1981 | Uson |
| 4,284,459 A | 8/1981 | Patel et al. |
| 4,287,227 A | 9/1981 | Kamada et al. |
| 4,306,557 A | 12/1981 | North |
| 4,311,146 A | 1/1982 | Wonder |
| 4,311,659 A | 1/1982 | Rey et al. |
| 4,318,406 A | 3/1982 | McLeod |
| 4,318,947 A | 3/1982 | Joung |
| 4,341,817 A | 7/1982 | Tozier et al. |
| 4,343,788 A | 8/1982 | Mustacich et al. |
| 4,350,161 A | 9/1982 | Davis, Jr. |
| 4,351,333 A | 9/1982 | Lazarus et al. |
| 4,366,901 A | 1/1983 | Short |
| 4,367,732 A | 1/1983 | Poulsen et al. |
| 4,378,018 A | 3/1983 | Alexander et al. |
| 4,378,796 A | 4/1983 | Milhaud |
| 4,379,506 A | 4/1983 | Davidson |
| 4,381,008 A | 4/1983 | Thomas et al. |
| 4,381,380 A | 4/1983 | LeVeen et al. |
| 4,392,848 A | 7/1983 | Lucas et al. |
| 4,395,806 A | 8/1983 | Wonder et al. |
| 4,411,648 A | 10/1983 | Davis et al. |
| 4,419,097 A | 12/1983 | Rowland |
| 4,428,365 A | 1/1984 | Hakky |
| 4,449,971 A | 5/1984 | Cawood |
| 4,457,299 A | 7/1984 | Cornwell |
| 4,472,226 A | 9/1984 | Redinger et al. |
| 4,475,910 A | 10/1984 | Conway et al. |
| 4,477,325 A | 10/1984 | Osburn |
| 4,479,795 A | 10/1984 | Mustacich et al. |
| 4,486,504 A | 12/1984 | Chung |
| 4,496,354 A | 1/1985 | Steer et al. |
| 4,515,593 A | 5/1985 | Norton |
| 4,517,971 A | 5/1985 | Sorbonne |
| 4,534,768 A | 8/1985 | Osburn et al. |
| 4,539,234 A | 9/1985 | Sakamoto et al. |
| 4,540,409 A | 9/1985 | Nystrom et al. |
| 4,552,269 A | 11/1985 | Chang |
| 4,553,533 A | 11/1985 | Leighton |
| 4,560,382 A | 12/1985 | Isono et al. |
| 4,563,184 A | 1/1986 | Korol |
| 4,568,340 A | 2/1986 | Giacalone |
| 4,571,239 A | 2/1986 | Heyman |
| 4,571,240 A | 2/1986 | Samson et al. |
| 4,571,241 A | 2/1986 | Christopher |
| 4,576,599 A | 3/1986 | Lipner |
| 4,581,026 A | 4/1986 | Schneider |
| 4,581,028 A | 4/1986 | Fox, Jr. et al. |
| 4,582,762 A | 4/1986 | Onohara et al. |
| 4,585,666 A | 4/1986 | Lambert |
| 4,586,974 A | 5/1986 | Nystrom et al. |
| 4,589,874 A | 5/1986 | Riedel et al. |
| 4,592,920 A | 6/1986 | Murtfeldt |
| 4,597,765 A | 7/1986 | Klatt |
| 4,597,931 A | 7/1986 | Watanabe et al. |
| 4,601,713 A | 7/1986 | Fuqua |
| 4,603,152 A | 7/1986 | Laurin et al. |
| 4,607,746 A | 8/1986 | Stinnette |
| 4,610,670 A | 9/1986 | Spencer |
| 4,612,337 A | 9/1986 | Fox, Jr. et al. |
| 4,613,324 A | 9/1986 | Ghajar |
| 4,615,692 A | 10/1986 | Giacalone et al. |
| 4,615,697 A | 10/1986 | Robinson |
| 4,619,642 A | 10/1986 | Spencer |
| 4,622,033 A | 11/1986 | Taniguchi |
| 4,623,329 A | 11/1986 | Drobish et al. |
| 4,626,250 A | 12/1986 | Schneider |
| 4,627,844 A | 12/1986 | Schmitt |
| 4,634,433 A | 1/1987 | Osborne |
| 4,637,907 A | 1/1987 | Hegel et al. |
| 4,638,790 A | 1/1987 | Conway et al. |
| 4,639,246 A | 1/1987 | Dudley |
| 4,640,688 A | 2/1987 | Hauser |
| 4,652,259 A | 3/1987 | O'Neil |
| 4,664,657 A | 5/1987 | Williamitis et al. |
| 4,673,401 A | 6/1987 | Jensen et al. |
| 4,677,143 A | 6/1987 | Laurin et al. |
| 4,681,572 A | 7/1987 | Tokarz et al. |
| 4,685,913 A | 8/1987 | Austin |
| 4,686,124 A | 8/1987 | Onohara et al. |
| 4,687,470 A | 8/1987 | Okada |
| 4,692,152 A | 9/1987 | Emde |
| 4,692,154 A | 9/1987 | Singery et al. |
| 4,696,672 A | 9/1987 | Mochizuki et al. |
| 4,699,616 A | 10/1987 | Nowak et al. |
| 4,704,102 A | 11/1987 | Guthery |
| 4,710,169 A | 12/1987 | Christopher |
| 4,710,181 A | 12/1987 | Fuqua |
| 4,723,946 A | 2/1988 | Kay |
| 4,731,064 A | 3/1988 | Heyden |
| 4,737,219 A | 4/1988 | Taller et al. |
| 4,738,667 A | 4/1988 | Galloway |
| 4,739,768 A | 4/1988 | Engelson |
| 4,747,845 A | 5/1988 | Korol |
| 4,754,877 A | 7/1988 | Johansson et al. |
| 4,759,753 A | 7/1988 | Schneider et al. |
| 4,762,128 A | 8/1988 | Rosenbluth |
| 4,769,013 A | 9/1988 | Lorenz et al. |
| 4,769,099 A | 9/1988 | Therriault et al. |
| 4,772,473 A | 9/1988 | Patel et al. |
| 4,773,901 A | 9/1988 | Norton |
| 4,775,371 A | 10/1988 | Mueller, Jr. |
| 4,784,651 A | 11/1988 | Hickey et al. |
| 4,790,834 A | 12/1988 | Austin |
| 4,790,835 A | 12/1988 | Elias |
| D299,865 S | 2/1989 | Kamstrup-Larsen et al. |
| 4,810,247 A | 3/1989 | Glassman |
| 4,811,847 A | 3/1989 | Reif et al. |
| 4,813,935 A | 3/1989 | Haber et al. |
| 4,820,270 A | 4/1989 | Hardcastle et al. |
| 4,820,289 A | 4/1989 | Coury et al. |
| 4,820,291 A | 4/1989 | Terauchi et al. |
| 4,820,292 A | 4/1989 | Korol et al. |
| 4,834,721 A | 5/1989 | Onohara et al. |
| 4,838,876 A | 6/1989 | Wong et al. |
| 4,846,784 A | 7/1989 | Haber |
| 4,846,909 A | 7/1989 | Klug et al. |
| 4,850,969 A | 7/1989 | Jackson |
| 4,861,337 A | 8/1989 | George |
| 4,863,424 A | 9/1989 | Blake, III et al. |
| 4,863,444 A | 9/1989 | Blomer |
| 4,863,449 A | 9/1989 | Therriault et al. |
| 4,867,748 A | 9/1989 | Samuelsen |
| 4,874,373 A | 10/1989 | Luther et al. |
| 4,876,109 A | 10/1989 | Mayer et al. |
| 4,885,049 A | 12/1989 | Johannesson |
| 4,886,508 A | 12/1989 | Washington |
| 4,888,005 A | 12/1989 | Dingeman et al. |
| 4,893,623 A | 1/1990 | Rosenbluth |
| 4,894,059 A | 1/1990 | Larsen et al. |
| 4,902,503 A | 2/1990 | Umemura et al. |
| 4,904,260 A | 2/1990 | Ray et al. |
| 4,917,113 A | 4/1990 | Conway et al. |
| 4,917,686 A | 4/1990 | Bayston et al. |
| RE33,206 E | 5/1990 | Conway et al. |
| 4,923,450 A | 5/1990 | Maeda et al. |
| 4,925,668 A | 5/1990 | Khan et al. |
| 4,930,522 A | 6/1990 | Busnel et al. |
| 4,931,056 A | 6/1990 | Ghajar et al. |
| 4,932,938 A | 6/1990 | Goldberg et al. |

(56)          References Cited

U.S. PATENT DOCUMENTS

| | | | |
|---|---|---|---|
| 4,932,948 A | 6/1990 | Kernes et al. |
| 4,934,999 A | 6/1990 | Bader |
| 4,935,260 A | 6/1990 | Shlenker |
| 4,950,256 A | 8/1990 | Luther et al. |
| 4,957,487 A | 9/1990 | Gerow |
| 4,963,137 A | 10/1990 | Heyden |
| 4,968,294 A | 11/1990 | Salama |
| 4,968,507 A | 11/1990 | Zentner et al. |
| 4,976,703 A | 12/1990 | Franetzki et al. |
| 4,981,471 A | 1/1991 | Quinn et al. |
| 4,994,047 A | 2/1991 | Walker et al. |
| 4,997,426 A | 3/1991 | Dingeman et al. |
| 5,001,009 A | 3/1991 | Whitbourne |
| 5,004,454 A | 4/1991 | Beyar et al. |
| 5,007,897 A | 4/1991 | Kalb et al. |
| 5,013,306 A | 5/1991 | Solomon et al. |
| 5,013,717 A | 5/1991 | Solomon et al. |
| 5,019,096 A | 5/1991 | Fox, Jr. et al. |
| 5,019,378 A | 5/1991 | Allen |
| 5,019,601 A | 5/1991 | Allen |
| 5,045,078 A | 9/1991 | Asta |
| 5,059,190 A | 10/1991 | Novak |
| 5,062,716 A | 11/1991 | Conrad et al. |
| 5,071,406 A | 12/1991 | Jang |
| 5,077,352 A | 12/1991 | Elton |
| 5,078,707 A | 1/1992 | Peter Klug |
| 5,082,006 A | 1/1992 | Jonasson |
| 5,084,037 A | 1/1992 | Barnett |
| 5,087,252 A | 2/1992 | Denard |
| 5,088,980 A | 2/1992 | Leighton |
| 5,089,205 A | 2/1992 | Huang et al. |
| 5,090,424 A | 2/1992 | Simon et al. |
| 5,098,379 A | 3/1992 | Conway et al. |
| 5,100,396 A | 3/1992 | Zamierowski |
| 5,102,401 A | 4/1992 | Lambert et al. |
| 5,102,405 A | 4/1992 | Conway et al. |
| 5,109,378 A | 4/1992 | Proctor et al. |
| 5,109,601 A | 5/1992 | McBride |
| 5,112,306 A | 5/1992 | Burton et al. |
| 5,114,398 A | 5/1992 | Trick et al. |
| 5,118,007 A | 6/1992 | Lewis et al. |
| 5,128,088 A | 7/1992 | Shimomura et al. |
| 5,131,906 A | 7/1992 | Chen |
| 5,137,671 A | 8/1992 | Conway et al. |
| 5,140,999 A | 8/1992 | Ardito |
| 5,147,341 A | 9/1992 | Starke et al. |
| 5,165,952 A | 11/1992 | Solomon et al. |
| 5,174,290 A | 12/1992 | Fiddian-Green |
| 5,176,666 A | 1/1993 | Conway et al. |
| 5,179,174 A | 1/1993 | Elton |
| 5,180,591 A | 1/1993 | Magruder et al. |
| 5,186,172 A | 2/1993 | Fiddian-Green |
| 5,188,596 A | 2/1993 | Condon et al. |
| 5,197,957 A | 3/1993 | Wendler |
| 5,201,724 A | 4/1993 | Hukins et al. |
| 5,209,726 A | 5/1993 | Goosen |
| 5,209,728 A | 5/1993 | Kraus et al. |
| 5,211,640 A | 5/1993 | Wendler |
| 5,224,953 A | 7/1993 | Morgentaler |
| 5,226,530 A | 7/1993 | Golden |
| 5,234,411 A | 8/1993 | Vaillancourt et al. |
| 5,236,422 A | 8/1993 | Eplett, Jr. |
| 5,242,391 A | 9/1993 | Place et al. |
| 5,242,398 A | 9/1993 | Knoll et al. |
| 5,242,428 A | 9/1993 | Palestrant |
| 5,261,896 A | 11/1993 | Conway et al. |
| 5,263,947 A | 11/1993 | Kay |
| 5,269,755 A | 12/1993 | Bodicky |
| 5,269,770 A | 12/1993 | Conway et al. |
| 5,270,358 A | 12/1993 | Asmus |
| 5,282,795 A | 2/1994 | Finney |
| 5,290,306 A | 3/1994 | Trotta et al. |
| 5,306,226 A | 4/1994 | Salama |
| 5,334,175 A | 8/1994 | Conway et al. |
| 5,336,211 A | 8/1994 | Metz |
| 5,346,483 A | 9/1994 | Thaxton, Sr. |
| 5,348,536 A | 9/1994 | Young et al. |
| 5,352,182 A | 10/1994 | Kalb et al. |
| 5,354,132 A | 10/1994 | Young et al. |
| 5,360,402 A | 11/1994 | Conway et al. |
| 5,360,414 A | 11/1994 | Yarger |
| 5,366,449 A | 11/1994 | Gilberg |
| 5,368,575 A | 11/1994 | Chang |
| 5,370,899 A | 12/1994 | Conway et al. |
| 5,376,085 A | 12/1994 | Conway et al. |
| 5,380,312 A | 1/1995 | Goulter |
| 5,395,333 A | 3/1995 | Brill |
| 5,409,014 A | 4/1995 | Napoli et al. |
| 5,409,495 A | 4/1995 | Osborn |
| 5,415,165 A | 5/1995 | Fiddian-Green |
| 5,415,635 A | 5/1995 | Bagaoisan et al. |
| 5,417,226 A | 5/1995 | Juma |
| 5,417,666 A | 5/1995 | Coulter |
| 5,423,784 A | 6/1995 | Metz |
| 5,433,705 A | 7/1995 | Giebel et al. |
| 5,433,713 A | 7/1995 | Trotta |
| 5,445,626 A | 8/1995 | Gigante et al. |
| 5,447,231 A | 9/1995 | Kastenhofer |
| 5,451,424 A | 9/1995 | Solomon et al. |
| 5,454,798 A | 10/1995 | Kubalak et al. |
| 5,456,251 A | 10/1995 | Fiddian-Green |
| 5,464,650 A | 11/1995 | Berg et al. |
| 5,466,229 A | 11/1995 | Elson et al. |
| 5,476,434 A | 12/1995 | Kalb et al. |
| 5,479,945 A | 1/1996 | Simon |
| 5,482,740 A | 1/1996 | Conway et al. |
| 5,483,976 A | 1/1996 | McLaughlin et al. |
| 5,497,601 A | 3/1996 | Gonzalez |
| 5,501,669 A | 3/1996 | Conway et al. |
| 5,509,427 A | 4/1996 | Simon et al. |
| 5,509,889 A | 4/1996 | Kalb et al. |
| 5,509,899 A | 4/1996 | Fan et al. |
| 5,513,659 A | 5/1996 | Buuck et al. |
| 5,513,660 A | 5/1996 | Simon et al. |
| 5,514,112 A | 5/1996 | Chu et al. |
| 5,520,636 A | 5/1996 | Korth et al. |
| 5,531,715 A | 7/1996 | Engelson et al. |
| 5,531,717 A | 7/1996 | Roberto et al. |
| 5,536,258 A | 7/1996 | Folden |
| 5,538,584 A | 7/1996 | Metz |
| 5,554,140 A | 9/1996 | Michels et al. |
| 5,554,141 A | 9/1996 | Wendler |
| 5,558,900 A | 9/1996 | Fan et al. |
| 5,562,599 A | 10/1996 | Beyschlag |
| 5,567,495 A | 10/1996 | Modak et al. |
| 5,569,219 A | 10/1996 | Hakki et al. |
| 5,582,599 A | 12/1996 | Daneshvar |
| 5,591,292 A | 1/1997 | Blomqvist |
| 5,593,718 A | 1/1997 | Conway et al. |
| 5,599,321 A | 2/1997 | Conway et al. |
| 5,601,537 A | 2/1997 | Frassica |
| 5,607,417 A | 3/1997 | Batich et al. |
| 5,614,143 A | 3/1997 | Hager |
| 5,616,126 A | 4/1997 | Malekmehr et al. |
| 5,620,109 A | 4/1997 | Madden |
| 5,624,395 A | 4/1997 | Mikhail et al. |
| 5,630,429 A | 5/1997 | Dann |
| 5,643,235 A | 7/1997 | Figuerido |
| 5,645,048 A | 7/1997 | Brodsky et al. |
| 5,653,700 A | 8/1997 | Byrne et al. |
| 5,670,111 A | 9/1997 | Conway et al. |
| 5,671,755 A | 9/1997 | Simon et al. |
| 5,688,516 A | 11/1997 | Raad et al. |
| 5,695,456 A | 12/1997 | Cartmell et al. |
| 5,695,485 A | 12/1997 | Duperret et al. |
| 5,702,381 A | 12/1997 | Cottenden |
| 5,704,353 A | 1/1998 | Kalb et al. |
| 5,707,357 A | 1/1998 | Mikhail et al. |
| 5,709,672 A | 1/1998 | Illner |
| 5,711,841 A | 1/1998 | Jaker |
| 5,724,994 A | 3/1998 | Simon et al. |
| 5,730,733 A | 3/1998 | Mortier et al. |
| 5,736,152 A | 4/1998 | Dunn |
| 5,749,826 A | 5/1998 | Faulkner |

(56) References Cited

U.S. PATENT DOCUMENTS

| | | | |
|---|---|---|---|
| 5,752,525 A | 5/1998 | Simon et al. |
| 5,756,144 A | 5/1998 | Wolff et al. |
| 5,762,996 A | 6/1998 | Lucas et al. |
| 5,779,670 A | 7/1998 | Bidwell et al. |
| 5,782,808 A | 7/1998 | Folden |
| 5,785,694 A | 7/1998 | Cohen et al. |
| 5,788,687 A | 8/1998 | Batich et al. |
| 5,789,018 A | 8/1998 | Engelson et al. |
| 5,795,332 A | 8/1998 | Lucas et al. |
| 5,795,334 A | 8/1998 | Cochrane, III |
| 5,795,524 A | 8/1998 | Basso, Jr. et al. |
| 5,800,339 A | 9/1998 | Salama |
| 5,806,527 A | 9/1998 | Borodulin et al. |
| 5,810,789 A | 9/1998 | Powers et al. |
| 5,817,067 A | 10/1998 | Tsukada et al. |
| 5,820,583 A | 10/1998 | Demopulos et al. |
| 5,820,607 A | 10/1998 | Tcholakian et al. |
| 5,827,247 A | 10/1998 | Kay |
| 5,827,249 A | 10/1998 | Jensen |
| 5,830,932 A | 11/1998 | Kay |
| 5,840,151 A | 11/1998 | Munsch |
| 5,848,691 A | 12/1998 | Morris et al. |
| 5,853,518 A | 12/1998 | Utas |
| 5,871,475 A | 2/1999 | Frassica |
| 5,877,243 A | 3/1999 | Sarangapani |
| 5,895,374 A | 4/1999 | Rodsten |
| 5,897,535 A | 4/1999 | Feliziani et al. |
| 5,902,631 A | 5/1999 | Wang et al. |
| 5,906,575 A | 5/1999 | Conway et al. |
| 5,919,170 A | 7/1999 | Woessner |
| 5,941,856 A | 8/1999 | Kovacs et al. |
| 5,958,167 A | 9/1999 | Van Driel et al. |
| 5,971,954 A | 10/1999 | Conway et al. |
| 5,980,483 A | 11/1999 | Dimitri |
| 5,980,507 A | 11/1999 | Fassuliotis et al. |
| 5,989,230 A | 11/1999 | Frassica |
| 5,997,517 A | 12/1999 | Whitbourne |
| 6,004,305 A | 12/1999 | Hursman et al. |
| 6,007,521 A | 12/1999 | Bidwell et al. |
| 6,007,524 A | 12/1999 | Schneider |
| 6,007,526 A | 12/1999 | Passalaqua et al. |
| 6,024,751 A | 2/2000 | Lovato et al. |
| 6,050,934 A | 4/2000 | Mikhail et al. |
| 6,053,905 A | 4/2000 | Daignault, Jr. et al. |
| 6,056,715 A | 5/2000 | Demopulos et al. |
| 6,059,107 A | 5/2000 | Nosted et al. |
| 6,063,063 A | 5/2000 | Harboe et al. |
| 6,065,597 A * | 5/2000 | Pettersson .......... A61M 25/0111 |
| | | 206/439 |
| 6,070,275 A | 6/2000 | Garlock |
| 6,090,075 A | 7/2000 | House |
| 6,097,976 A | 8/2000 | Yang et al. |
| 6,102,929 A | 8/2000 | Conway et al. |
| 6,113,582 A | 9/2000 | Dwork |
| 6,119,697 A | 9/2000 | Engel et al. |
| 6,131,575 A | 10/2000 | Lenker et al. |
| 6,132,399 A | 10/2000 | Shultz |
| 6,156,049 A | 12/2000 | Lovato et al. |
| 6,162,201 A | 12/2000 | Cohen et al. |
| 6,183,461 B1 | 2/2001 | Matsuura et al. |
| 6,186,990 B1 | 2/2001 | Chen et al. |
| 6,190,353 B1 | 2/2001 | Makower et al. |
| 6,206,885 B1 | 3/2001 | Ghahremani et al. |
| 6,210,394 B1 | 4/2001 | Demopulos et al. |
| 6,217,569 B1 | 4/2001 | Fiore |
| 6,221,056 B1 | 4/2001 | Silverman |
| 6,231,501 B1 | 5/2001 | Ditter |
| 6,238,383 B1 | 5/2001 | Karram et al. |
| 6,254,570 B1 | 7/2001 | Rutner et al. |
| 6,254,582 B1 | 7/2001 | O'Donnell et al. |
| 6,254,585 B1 | 7/2001 | Demopulos et al. |
| 6,256,525 B1 | 7/2001 | Yang et al. |
| 6,261,255 B1 | 7/2001 | Mullis et al. |
| 6,261,271 B1 | 7/2001 | Solomon et al. |
| 6,261,279 B1 | 7/2001 | Demopulos et al. |
| 6,270,902 B1 | 8/2001 | Tedeschi et al. |
| 6,280,425 B1 | 8/2001 | Del Guercio |
| 6,287,285 B1 | 9/2001 | Michal et al. |
| 6,293,923 B1 | 9/2001 | Yachia et al. |
| 6,296,627 B1 | 10/2001 | Edwards |
| 6,299,598 B1 | 10/2001 | Bander |
| 6,306,176 B1 | 10/2001 | Whitbourne |
| 6,306,422 B1 | 10/2001 | Batich et al. |
| 6,309,104 B1 | 10/2001 | Koch et al. |
| 6,315,711 B1 | 11/2001 | Conway et al. |
| 6,329,488 B1 | 12/2001 | Terry et al. |
| 6,340,359 B1 | 1/2002 | Silverman |
| 6,340,465 B1 | 1/2002 | Hsu et al. |
| 6,355,004 B1 | 3/2002 | Pedersen et al. |
| 6,358,229 B1 | 3/2002 | Tihon |
| 6,368,315 B1 | 4/2002 | Gillis et al. |
| 6,368,317 B2 | 4/2002 | Chang |
| 6,379,334 B1 | 4/2002 | Frassica |
| 6,383,434 B2 | 5/2002 | Conway et al. |
| 6,387,080 B1 | 5/2002 | Rodsten |
| 6,391,010 B1 | 5/2002 | Wilcox |
| 6,391,014 B1 | 5/2002 | Silverman |
| 6,398,718 B1 | 6/2002 | Yachia et al. |
| 6,402,726 B1 | 6/2002 | Genese |
| 6,409,717 B1 | 6/2002 | Israelsson et al. |
| 6,423,041 B1 | 7/2002 | Grant |
| 6,437,038 B1 | 8/2002 | Chen |
| 6,440,060 B1 | 8/2002 | Latour, Jr. |
| 6,458,867 B1 | 10/2002 | Wang et al. |
| 6,468,245 B2 | 10/2002 | Alexandersen |
| 6,479,000 B2 | 11/2002 | Conway et al. |
| 6,479,726 B1 | 11/2002 | Cole |
| 6,485,476 B1 | 11/2002 | von Dyck et al. |
| 6,509,319 B1 | 1/2003 | Raad et al. |
| 6,544,240 B1 | 4/2003 | Borodulin et al. |
| 6,551,293 B1 | 4/2003 | Mitchell |
| 6,558,369 B2 | 5/2003 | Rosenblum |
| 6,558,792 B1 | 5/2003 | Vaabengaard et al. |
| 6,558,798 B2 | 5/2003 | Zhong et al. |
| 6,578,709 B1 | 6/2003 | Kavanagh et al. |
| 6,579,539 B2 | 6/2003 | Lawson et al. |
| 6,582,401 B1 | 6/2003 | Windheuser et al. |
| 6,596,401 B1 | 7/2003 | Terry et al. |
| 6,602,244 B2 | 8/2003 | Kavanagh et al. |
| 6,613,014 B1 | 9/2003 | Chi |
| 6,613,342 B2 | 9/2003 | Aoki |
| 6,626,888 B1 | 9/2003 | Conway et al. |
| 6,629,969 B2 | 10/2003 | Chan et al. |
| 6,632,204 B2 | 10/2003 | Guldfeldt et al. |
| 6,634,498 B2 | 10/2003 | Kayerod et al. |
| 6,638,269 B2 | 10/2003 | Wilcox |
| 6,648,906 B2 | 11/2003 | Lasheras et al. |
| 6,659,937 B2 | 12/2003 | Polsky et al. |
| 6,682,555 B2 | 1/2004 | Cioanta et al. |
| 6,693,189 B2 | 2/2004 | Holt et al. |
| 6,695,831 B1 | 2/2004 | Tsukada et al. |
| 6,706,025 B2 | 3/2004 | Engelson et al. |
| 6,711,436 B1 | 3/2004 | Duhaylongsod |
| 6,716,895 B1 | 4/2004 | Terry |
| 6,719,709 B2 | 4/2004 | Whalen et al. |
| 6,723,350 B2 | 4/2004 | Burrell et al. |
| 6,730,113 B2 | 5/2004 | Eckhardt et al. |
| 6,733,474 B2 | 5/2004 | Kusleika |
| 6,736,805 B2 | 5/2004 | Israelsson et al. |
| 6,740,273 B2 | 5/2004 | Lee |
| 6,746,421 B2 | 6/2004 | Yachia et al. |
| 6,767,551 B2 | 7/2004 | McGhee et al. |
| 6,780,504 B2 | 8/2004 | Rupprecht et al. |
| 6,783,520 B1 | 8/2004 | Candray et al. |
| D496,266 S | 9/2004 | Nestenborg |
| 6,787,156 B1 | 9/2004 | Bar-Shalom |
| 6,797,743 B2 | 9/2004 | McDonald et al. |
| 6,824,532 B2 | 11/2004 | Gillis et al. |
| 6,835,183 B2 | 12/2004 | Lennox et al. |
| 6,835,410 B2 | 12/2004 | Chabrecek et al. |
| 6,840,379 B2 | 1/2005 | Franks-Farah et al. |
| 6,848,574 B1 | 2/2005 | Israelsson et al. |
| 6,849,070 B1 | 2/2005 | Hansen et al. |
| 6,852,098 B2 | 2/2005 | Byrne |

(56) References Cited

U.S. PATENT DOCUMENTS

| | | | |
|---|---|---|---|
| 6,852,105 | B2 | 2/2005 | Bolmsjo et al. |
| D503,335 | S | 3/2005 | Risberg et al. |
| 6,869,416 | B2 | 3/2005 | Windheuser et al. |
| 6,872,195 | B2 | 3/2005 | Modak et al. |
| 6,887,223 | B2 | 5/2005 | Bisbee |
| 6,887,230 | B2 | 5/2005 | Kubalak et al. |
| 6,889,740 | B1 | 5/2005 | Globensky et al. |
| 6,918,924 | B2 | 7/2005 | Lasheras et al. |
| 6,926,708 | B1 | 8/2005 | Franks-Farah et al. |
| 6,939,339 | B1 | 9/2005 | Axexandersen et al. |
| 6,939,554 | B2 | 9/2005 | McDonald et al. |
| 6,941,171 | B2 | 9/2005 | Mann et al. |
| 6,942,634 | B2 | 9/2005 | Odland |
| 6,945,957 | B2 | 9/2005 | Freyman |
| 6,949,598 | B2 | 9/2005 | Terry |
| 6,951,902 | B2 | 10/2005 | McDonald et al. |
| 6,972,040 | B2 | 12/2005 | Rioux et al. |
| 7,001,370 | B2 | 2/2006 | Kubalak et al. |
| 7,033,367 | B2 | 4/2006 | Ghahremani et al. |
| 7,048,717 | B1 | 5/2006 | Frassica |
| 7,059,330 | B1 | 6/2006 | Makower et al. |
| 7,066,912 | B2 | 6/2006 | Nestenborg et al. |
| 7,087,041 | B2 | 8/2006 | von Dyck et al. |
| 7,087,048 | B2 | 8/2006 | Israelsson et al. |
| 7,094,220 | B2 | 8/2006 | Tanghoj et al. |
| 7,112,298 | B2 | 9/2006 | Kampa et al. |
| 7,160,277 | B2 | 1/2007 | Elson et al. |
| 7,166,092 | B2 | 1/2007 | Elson et al. |
| 7,195,608 | B2 | 3/2007 | Burnett |
| 7,204,940 | B2 | 4/2007 | McDonald et al. |
| 7,211,275 | B2 | 5/2007 | Mng et al. |
| 7,244,242 | B2 | 7/2007 | Freyman |
| 7,250,043 | B2 | 7/2007 | Chan et al. |
| 7,255,687 | B2 | 8/2007 | Huang et al. |
| 7,270,647 | B2 | 9/2007 | Karpowicz et al. |
| 7,294,117 | B2 | 11/2007 | Provost-Tine et al. |
| 7,311,690 | B2 | 12/2007 | Burnett |
| 7,311,698 | B2 | 12/2007 | Tanghoj et al. |
| 7,329,412 | B2 | 2/2008 | Modak et al. |
| 7,331,948 | B2 | 2/2008 | Skarda |
| 7,334,679 | B2 | 2/2008 | Givens, Jr. |
| 7,374,040 | B2 | 5/2008 | Lee et al. |
| 7,380,658 | B2 | 6/2008 | Murray et al. |
| 7,402,559 | B2 | 7/2008 | Catania et al. |
| 7,445,812 | B2 | 11/2008 | Schmidt et al. |
| 7,458,964 | B2 | 12/2008 | Mosler et al. |
| 7,476,223 | B2 | 1/2009 | McBride |
| 7,507,229 | B2 | 3/2009 | Hewitt et al. |
| 7,517,343 | B2 | 4/2009 | Tanghoj et al. |
| 7,537,589 | B2 | 5/2009 | Tsukada et al. |
| 7,571,804 | B2 | 8/2009 | Kjellmann Bruun et al. |
| 7,601,158 | B2 | 10/2009 | House |
| 7,615,045 | B2 | 11/2009 | Israelsson et al. |
| 7,628,784 | B2 | 12/2009 | Diaz et al. |
| 7,632,256 | B2 | 12/2009 | Mosler et al. |
| D609,819 | S | 2/2010 | Tomes et al. |
| 7,662,146 | B2 | 2/2010 | House |
| 7,670,331 | B2 | 3/2010 | Tanghoej |
| 7,682,353 | B2 | 3/2010 | Tanghoj et al. |
| 7,682,669 | B1 | 3/2010 | Michal et al. |
| 7,691,091 | B1 | 4/2010 | Baggett |
| 7,691,476 | B2 | 4/2010 | Finley |
| 7,717,902 | B2 | 5/2010 | Sauer |
| 7,749,529 | B2 | 7/2010 | Ash et al. |
| 7,770,726 | B2 | 8/2010 | Murray et al. |
| 7,770,728 | B2 | 8/2010 | Kaern |
| 7,780,640 | B1 | 8/2010 | Amador |
| 7,780,642 | B2 | 8/2010 | Rasmussen et al. |
| 7,789,873 | B2 | 9/2010 | Kubalak et al. |
| 7,820,734 | B2 | 10/2010 | McGhee |
| 7,823,722 | B2 | 11/2010 | Bezou et al. |
| 7,846,133 | B2 | 12/2010 | Windheuser et al. |
| 7,867,220 | B2 | 1/2011 | Tanghoj |
| 7,886,907 | B2 | 2/2011 | Murray et al. |
| 7,896,857 | B2 | 3/2011 | Kay et al. |
| 7,918,831 | B2 | 4/2011 | House |
| 7,938,838 | B2 | 5/2011 | House |
| 7,947,021 | B2 | 5/2011 | Bourne et al. |
| 7,985,217 | B2 | 7/2011 | Mosler et al. |
| 8,007,464 | B2 | 8/2011 | Gellman |
| 8,011,505 | B2 | 9/2011 | Murray et al. |
| 8,051,981 | B2 | 11/2011 | Murray et al. |
| 8,052,673 | B2 | 11/2011 | Nestenborg |
| 8,053,030 | B2 | 11/2011 | Gilman |
| 8,066,693 | B2 | 11/2011 | Tanghoj et al. |
| 8,127,922 | B2 | 3/2012 | Nordholm et al. |
| 8,133,580 | B2 | 3/2012 | Dias et al. |
| 8,163,327 | B2 | 4/2012 | Finley |
| 8,177,774 | B2 | 5/2012 | House |
| 8,181,778 | B1 | 5/2012 | van Groningen et al. |
| 8,192,413 | B2 | 6/2012 | Bjerregaard |
| 8,201,689 | B2 | 6/2012 | Kaern |
| 8,205,745 | B2 | 6/2012 | Murray et al. |
| 8,207,393 | B2 | 6/2012 | Bach |
| 8,230,993 | B2 | 7/2012 | Tanghoej |
| 8,267,919 | B2 | 9/2012 | Utas et al. |
| 8,282,624 | B2 | 10/2012 | Tanghoej et al. |
| 8,287,519 | B2 | 10/2012 | Smith |
| 8,287,890 | B2 | 10/2012 | Elton |
| 8,298,202 | B2 | 10/2012 | McCray |
| 8,303,556 | B2 | 11/2012 | White |
| 8,317,775 | B2 | 11/2012 | House |
| 8,328,792 | B2 | 12/2012 | Nishtala et al. |
| 8,356,457 | B2 | 1/2013 | Murray et al. |
| 8,377,498 | B2 | 2/2013 | Rindlav-Westling et al. |
| 8,377,559 | B2 | 2/2013 | Gilman |
| 8,382,708 | B2 | 2/2013 | Mayback et al. |
| 8,398,615 | B2 | 3/2013 | Torstensen et al. |
| 8,409,171 | B2 | 4/2013 | Hannon et al. |
| 8,454,569 | B2 | 6/2013 | Kull-Osterlin et al. |
| 8,459,455 | B2 | 6/2013 | Frojd |
| 8,475,434 | B2 | 7/2013 | Frojd |
| 8,523,843 | B2 | 9/2013 | Kavanagh et al. |
| 8,556,884 | B2 | 10/2013 | Hong et al. |
| 8,608,718 | B1 | 12/2013 | Patterson-Young |
| 8,668,683 | B2 | 3/2014 | Golden |
| 8,720,685 | B2 | 5/2014 | Murray et al. |
| 8,805,533 | B2 | 8/2014 | Boggs et al. |
| 8,871,869 | B2 | 10/2014 | Dias et al. |
| 8,888,747 | B2 | 11/2014 | House |
| 8,919,553 | B2 | 12/2014 | Murray et al. |
| 8,974,438 | B2 | 3/2015 | Hong et al. |
| 8,998,882 | B2 | 4/2015 | Knapp et al. |
| 9,033,149 | B2 | 5/2015 | Terry |
| 9,072,862 | B2 | 7/2015 | Murray et al. |
| 9,078,760 | B2 | 7/2015 | Marshall |
| 9,108,020 | B1 | 8/2015 | Feloney |
| 9,114,227 | B2 | 8/2015 | Blanchard |
| 9,138,510 | B2 | 9/2015 | Madsen |
| 9,144,659 | B2 | 9/2015 | Tanghoj |
| 9,168,354 | B2 | 10/2015 | Hannon et al. |
| 9,186,438 | B2 | 11/2015 | Gravesen et al. |
| 9,192,506 | B2 | 11/2015 | Tanghoej et al. |
| 9,192,740 | B2 | 11/2015 | Frojd |
| 9,199,057 | B2 | 12/2015 | Nielsen |
| 9,205,222 | B2 | 12/2015 | Tanghoj |
| 9,220,866 | B2 | 12/2015 | Van Groningen et al. |
| 9,289,575 | B2 | 3/2016 | Dye |
| 9,314,585 | B2 | 4/2016 | Nestenborg et al. |
| 9,345,855 | B2 | 5/2016 | Young |
| 9,511,204 | B2 | 12/2016 | Tanghøj |
| 9,561,889 | B2 | 2/2017 | Dayrit et al. |
| 9,649,472 | B2 | 5/2017 | Kearns et al. |
| 9,669,187 | B2 | 6/2017 | Tjassens et al. |
| 9,687,628 | B2 | 6/2017 | Paz |
| 9,694,113 | B2 | 7/2017 | Knapp et al. |
| 9,694,157 | B2 | 7/2017 | Palmer |
| 9,707,375 | B2 | 7/2017 | Conway et al. |
| 9,731,093 | B2 | 8/2017 | Terry |
| 9,775,965 | B2 | 10/2017 | Tanghoej et al. |
| 9,801,979 | B2 | 10/2017 | Utas et al. |
| 9,821,139 | B2 | 11/2017 | Carleo |
| 9,872,969 | B2 | 1/2018 | Conway et al. |
| 9,884,167 | B2 | 2/2018 | Gustavsson |

(56) References Cited

U.S. PATENT DOCUMENTS

| | | |
|---|---|---|
| 9,918,869 B2 | 3/2018 | Henry et al. |
| 9,937,334 B2 | 4/2018 | Fröjd et al. |
| 10,112,031 B2 | 10/2018 | Matthiassen |
| 10,118,019 B2 | 11/2018 | Murray et al. |
| 10,149,961 B2 | 12/2018 | Carleo |
| 10,166,366 B2 | 1/2019 | Murray et al. |
| 10,179,676 B1 | 1/2019 | Taylor |
| 10,207,076 B2 | 2/2019 | Foley et al. |
| 10,265,499 B2 | 4/2019 | Hong et al. |
| 10,328,237 B2 | 6/2019 | Kelly et al. |
| 10,406,322 B2 | 9/2019 | O'Flynn et al. |
| 10,441,454 B2 | 10/2019 | Tanghoej et al. |
| 10,449,328 B2 | 10/2019 | Tanghoej et al. |
| 10,449,329 B2 | 10/2019 | Foley et al. |
| 10,518,000 B2 | 12/2019 | Knapp et al. |
| 10,561,817 B2 | 2/2020 | Hannon et al. |
| 10,569,046 B2 | 2/2020 | Steindahl et al. |
| 10,569,051 B2 | 2/2020 | Conway et al. |
| 10,639,451 B2 | 5/2020 | Kearns et al. |
| 10,646,688 B2 | 5/2020 | Hannon et al. |
| 10,702,671 B2 | 7/2020 | Terry |
| 10,758,704 B2 | 9/2020 | Hickmott et al. |
| 10,765,833 B2 | 9/2020 | Kearns |
| 10,857,324 B2 | 12/2020 | Mn et al. |
| 10,874,825 B2 | 12/2020 | Mn et al. |
| RE48,426 E | 2/2021 | Murray et al. |
| 10,912,917 B2 | 2/2021 | Terry |
| 11,020,561 B2 | 6/2021 | O'Brien et al. |
| 11,103,676 B2 | 8/2021 | McMenamin et al. |
| 11,129,961 B2 | 9/2021 | O'Flynn |
| 11,141,562 B2 | 10/2021 | McMenamin et al. |
| 11,154,688 B2 | 10/2021 | Schertiger |
| 11,167,107 B2 | 11/2021 | Schertiger et al. |
| 11,235,130 B2 | 2/2022 | Murray et al. |
| 11,241,566 B1 | 2/2022 | Lindsay |
| 11,253,675 B2 | 2/2022 | Fletter |
| 11,344,702 B2 | 5/2022 | Subramaniam et al. |
| 11,400,257 B2 | 8/2022 | Tierney et al. |
| 11,420,017 B2 | 8/2022 | Hilton et al. |
| 11,534,573 B2 | 12/2022 | Hannon et al. |
| 11,547,833 B2 | 1/2023 | Murray et al. |
| 11,607,524 B2 | 3/2023 | Conway et al. |
| 11,660,385 B1 | 5/2023 | Thakore et al. |
| 12,076,506 B2 | 9/2024 | Palmer |
| 12,383,700 B2 | 8/2025 | Murray et al. |
| 2001/0001443 A1 | 5/2001 | Kayerod et al. |
| 2001/0027299 A1 | 10/2001 | Yang et al. |
| 2001/0031933 A1 | 10/2001 | Cannon |
| 2001/0031952 A1 | 10/2001 | Karram et al. |
| 2001/0047147 A1 | 11/2001 | Slepian et al. |
| 2001/0054562 A1 | 12/2001 | Pettersson et al. |
| 2002/0007175 A1 | 1/2002 | Chang |
| 2002/0032406 A1 | 3/2002 | Kusleika |
| 2002/0037943 A1 | 3/2002 | Madsen |
| 2002/0045855 A1 | 4/2002 | Frassica |
| 2002/0055730 A1 | 5/2002 | Yachia et al. |
| 2002/0077611 A1 | 6/2002 | von Dyck et al. |
| 2002/0082551 A1 | 6/2002 | Yachia et al. |
| 2002/0087131 A1 | 7/2002 | Wolff et al. |
| 2002/0094322 A1 | 7/2002 | Lawson et al. |
| 2002/0095133 A1 | 7/2002 | Gillis et al. |
| 2002/0099356 A1 | 7/2002 | Unger et al. |
| 2002/0103467 A1 | 8/2002 | Kubalak |
| 2002/0107467 A1 | 8/2002 | Levin |
| 2002/0132013 A1 | 9/2002 | Moulis |
| 2002/0132049 A1 | 9/2002 | Leonard et al. |
| 2002/0133130 A1 | 9/2002 | Wilcox |
| 2002/0156440 A1 | 10/2002 | Israelsson et al. |
| 2002/0165427 A1 | 11/2002 | Yachia et al. |
| 2002/0169438 A1 | 11/2002 | Sauer |
| 2002/0182265 A1 | 12/2002 | Burrell et al. |
| 2003/0004496 A1 | 1/2003 | Tanghoj |
| 2003/0018293 A1 | 1/2003 | Tanghoj et al. |
| 2003/0018302 A1 | 1/2003 | Kavanagh et al. |
| 2003/0018322 A1 | 1/2003 | Tanghoj et al. |
| 2003/0023222 A1 | 1/2003 | Chen |
| 2003/0028174 A1 | 2/2003 | Chan et al. |
| 2003/0036802 A1 | 2/2003 | Lennox et al. |
| 2003/0055403 A1 | 3/2003 | Nestenborg et al. |
| 2003/0060807 A1 | 3/2003 | Tanghoj et al. |
| 2003/0065292 A1 | 4/2003 | Darouiche et al. |
| 2003/0083644 A1 | 5/2003 | Avaltroni |
| 2003/0130646 A1 | 7/2003 | Kubalak et al. |
| 2003/0132307 A1 | 7/2003 | Park |
| 2003/0135200 A1 | 7/2003 | Byrne |
| 2003/0163079 A1 | 8/2003 | Burnett |
| 2003/0168365 A1 | 9/2003 | Kaern |
| 2003/0195478 A1 | 10/2003 | Russo |
| 2003/0225392 A1 | 12/2003 | McMichael et al. |
| 2003/0233084 A1 | 12/2003 | Slepian et al. |
| 2004/0030301 A1 | 2/2004 | Hunter |
| 2004/0034329 A1 | 2/2004 | Mankus et al. |
| 2004/0044307 A1 | 3/2004 | Richardson et al. |
| 2004/0049152 A1 | 3/2004 | Nayak |
| 2004/0049170 A1 | 3/2004 | Snell |
| 2004/0055925 A1 | 3/2004 | Franks-Farah et al. |
| 2004/0059280 A1 | 3/2004 | Makower et al. |
| 2004/0068251 A1 | 4/2004 | Chan et al. |
| 2004/0074794 A1 | 4/2004 | Conway et al. |
| 2004/0097892 A1 | 5/2004 | Evans et al. |
| 2004/0116551 A1 | 6/2004 | Terry |
| 2004/0122382 A1 | 6/2004 | Johnson et al. |
| 2004/0127848 A1 | 7/2004 | Freyman |
| 2004/0133156 A1 | 7/2004 | Diaz et al. |
| 2004/0147871 A1 | 7/2004 | Burnett |
| 2004/0153049 A1 | 8/2004 | Hewitt et al. |
| 2004/0153051 A1 | 8/2004 | Israelsson et al. |
| 2004/0158231 A1 | 8/2004 | Tanghoj et al. |
| 2004/0163980 A1 | 8/2004 | Tanghoj et al. |
| 2004/0176747 A1 | 9/2004 | Feneley |
| 2004/0193143 A1 | 9/2004 | Sauer |
| 2004/0234572 A1 | 11/2004 | Martinod et al. |
| 2004/0236293 A1 | 11/2004 | Tanghoj et al. |
| 2004/0243104 A1 | 12/2004 | Seddon |
| 2004/0249343 A1 | 12/2004 | Cioanta |
| 2004/0254562 A1 | 12/2004 | Tanghoj et al. |
| 2004/0256264 A1 | 12/2004 | Israelsson et al. |
| 2005/0003118 A1 | 1/2005 | Takala |
| 2005/0011790 A1 | 1/2005 | Harrold |
| 2005/0015076 A1 | 1/2005 | Giebmeyer et al. |
| 2005/0031872 A1 | 2/2005 | Schmidt et al. |
| 2005/0033222 A1 | 2/2005 | Haggstrom et al. |
| 2005/0043715 A1 | 2/2005 | Nestenborg et al. |
| 2005/0049577 A1 | 3/2005 | Snell et al. |
| 2005/0059990 A1 | 3/2005 | Ayala et al. |
| 2005/0065499 A1 | 3/2005 | Douk et al. |
| 2005/0070882 A1 | 3/2005 | McBride |
| 2005/0080399 A1 | 4/2005 | Bolmsjo et al. |
| 2005/0096582 A1 | 5/2005 | Burnett |
| 2005/0101923 A1 | 5/2005 | Elson et al. |
| 2005/0101924 A1 | 5/2005 | Elson et al. |
| 2005/0107735 A1 | 5/2005 | Lennox et al. |
| 2005/0107771 A1 | 5/2005 | Finkbeiner |
| 2005/0109648 A1 | 5/2005 | Kerzman et al. |
| 2005/0137522 A1 | 6/2005 | Aoki |
| 2005/0137582 A1 | 6/2005 | Kull-Osterlin et al. |
| 2005/0143690 A1 | 6/2005 | High |
| 2005/0148950 A1 | 7/2005 | Windheuser et al. |
| 2005/0177104 A1 | 8/2005 | Conway |
| 2005/0197531 A1 | 9/2005 | Cabiri et al. |
| 2005/0199521 A1 | 9/2005 | Givens |
| 2005/0209580 A1 | 9/2005 | Freyman |
| 2005/0214443 A1 | 9/2005 | Madsen |
| 2005/0245901 A1 | 11/2005 | Floyd |
| 2005/0251108 A1 | 11/2005 | Frassica |
| 2005/0256447 A1 | 11/2005 | Richardson et al. |
| 2005/0273034 A1 | 12/2005 | Burnett |
| 2005/0282977 A1 | 12/2005 | Stempel et al. |
| 2005/0283136 A1 | 12/2005 | Skarda |
| 2006/0025753 A1 | 2/2006 | Kubalak et al. |
| 2006/0027854 A1 | 2/2006 | Kim et al. |
| 2006/0030864 A1 | 2/2006 | Kennedy, et al. |
| 2006/0036208 A1 | 2/2006 | Burnett |
| 2006/0041246 A1 | 2/2006 | Provost-Tine et al. |

(56)  References Cited

U.S. PATENT DOCUMENTS

| | | |
|---|---|---|
| 2006/0054557 A1 | 3/2006 | Hori et al. |
| 2006/0058777 A1 | 3/2006 | Nielsen |
| 2006/0064065 A1 | 3/2006 | Russo |
| 2006/0079835 A1 | 4/2006 | Frassica |
| 2006/0079854 A1 | 4/2006 | Kay et al. |
| 2006/0100511 A1 | 5/2006 | Eriksen |
| 2006/0122566 A1 | 6/2006 | Huang et al. |
| 2006/0122568 A1 | 6/2006 | Elson et al. |
| 2006/0142737 A1 | 6/2006 | Tanghoj |
| 2006/0172096 A1 | 8/2006 | Kyle et al. |
| 2006/0184112 A1 | 8/2006 | Horn et al. |
| 2006/0184145 A1 | 8/2006 | Ciok et al. |
| 2006/0189962 A1 | 8/2006 | Burtoft |
| 2006/0196783 A1 | 9/2006 | Bruun et al. |
| 2006/0200079 A1 | 9/2006 | Magnusson |
| 2006/0229576 A1 | 10/2006 | Conway et al. |
| 2006/0240069 A1 | 10/2006 | Utas et al. |
| 2006/0263404 A1 | 11/2006 | Nielsen et al. |
| 2006/0271019 A1 | 11/2006 | Stoller et al. |
| 2006/0276894 A1 | 12/2006 | Finley |
| 2006/0278546 A1 | 12/2006 | State et al. |
| 2006/0293642 A1 | 12/2006 | Israelsson et al. |
| 2007/0005024 A1 | 1/2007 | Weber et al. |
| 2007/0005041 A1 | 1/2007 | Frassica et al. |
| 2007/0010798 A1 | 1/2007 | Stoller et al. |
| 2007/0016168 A1 | 1/2007 | Conway |
| 2007/0016169 A1 | 1/2007 | Utas et al. |
| 2007/0049879 A1 | 3/2007 | Gutierrez |
| 2007/0059350 A1 | 3/2007 | Kennedy et al. |
| 2007/0066963 A1 | 3/2007 | Tanghoj |
| 2007/0084749 A1 | 4/2007 | Demelo et al. |
| 2007/0088330 A1 | 4/2007 | House |
| 2007/0106233 A1 | 5/2007 | Huang et al. |
| 2007/0108076 A1 | 5/2007 | Miller et al. |
| 2007/0112327 A1 | 5/2007 | Yun et al. |
| 2007/0112333 A1 | 5/2007 | Hoang et al. |
| 2007/0149929 A1 | 6/2007 | Utas et al. |
| 2007/0161971 A1 | 7/2007 | House |
| 2007/0197957 A1 | 8/2007 | Hunter et al. |
| 2007/0218102 A1 | 9/2007 | Chudzik et al. |
| 2007/0225635 A1 | 9/2007 | Lynn |
| 2007/0225649 A1 | 9/2007 | House |
| 2007/0225687 A1 | 9/2007 | House |
| 2007/0244449 A1 | 10/2007 | Najafi et al. |
| 2007/0287800 A1 | 12/2007 | Acquarulo et al. |
| 2007/0289887 A1 | 12/2007 | Murray et al. |
| 2008/0006554 A1 | 1/2008 | Duffy et al. |
| 2008/0015518 A1 | 1/2008 | Huang et al. |
| 2008/0015527 A1 | 1/2008 | House |
| 2008/0021382 A1 | 1/2008 | Freyman |
| 2008/0027414 A1 | 1/2008 | Tanghoj et al. |
| 2008/0033471 A1 | 2/2008 | Paz et al. |
| 2008/0050446 A1 | 2/2008 | Ziegler et al. |
| 2008/0051762 A1 | 2/2008 | Tsukada et al. |
| 2008/0051763 A1 | 2/2008 | Frojd |
| 2008/0063324 A1 | 3/2008 | Bernard et al. |
| 2008/0077099 A1 | 3/2008 | House |
| 2008/0082051 A1 | 4/2008 | Miller et al. |
| 2008/0085949 A1 | 4/2008 | McGhee |
| 2008/0086008 A1 | 4/2008 | Lhermitte et al. |
| 2008/0091145 A1 | 4/2008 | House |
| 2008/0097362 A1 | 4/2008 | Mosler et al. |
| 2008/0097394 A1 | 4/2008 | Lampropoulos et al. |
| 2008/0097411 A1 | 4/2008 | House |
| 2008/0103464 A1 | 5/2008 | Mosler et al. |
| 2008/0119803 A1 | 5/2008 | Lund |
| 2008/0125513 A1 | 5/2008 | Kristiansen |
| 2008/0140010 A1 | 6/2008 | Kennedy et al. |
| 2008/0140052 A1 | 6/2008 | Moller et al. |
| 2008/0171973 A1 | 7/2008 | House |
| 2008/0171998 A1 | 7/2008 | House |
| 2008/0172016 A1 | 7/2008 | House |
| 2008/0172040 A1 | 7/2008 | Smith |
| 2008/0172042 A1 | 7/2008 | House |
| 2008/0177217 A1 | 7/2008 | Polaschegg |
| 2008/0179208 A1 | 7/2008 | Murray et al. |
| 2008/0183262 A1 | 7/2008 | Dowling |
| 2008/0193497 A1 | 8/2008 | Samuelsen et al. |
| 2008/0200907 A1 | 8/2008 | Nestenborg |
| 2008/0215021 A1 | 9/2008 | Cisko, Jr. et al. |
| 2008/0243081 A1 | 10/2008 | Nance et al. |
| 2008/0243091 A1 | 10/2008 | Humphreys et al. |
| 2008/0249467 A1 | 10/2008 | Burnett et al. |
| 2008/0249482 A1 | 10/2008 | Erez |
| 2008/0275463 A1 | 11/2008 | High |
| 2008/0279907 A1 | 11/2008 | Ash et al. |
| 2008/0281291 A1 | 11/2008 | Tihon et al. |
| 2009/0000970 A1 | 1/2009 | Bordeau et al. |
| 2009/0005725 A1 | 1/2009 | Shorey |
| 2009/0012208 A1 | 1/2009 | Madsen et al. |
| 2009/0024111 A1 | 1/2009 | Borodulin et al. |
| 2009/0043287 A1 | 2/2009 | Mosler et al. |
| 2009/0048537 A1 | 2/2009 | Lydon et al. |
| 2009/0048570 A1 | 2/2009 | Jensen |
| 2009/0054876 A1 | 2/2009 | Borodulin et al. |
| 2009/0062754 A1 | 3/2009 | Tang |
| 2009/0065605 A1 | 3/2009 | Roche et al. |
| 2009/0071851 A1 | 3/2009 | Maki et al. |
| 2009/0099532 A1 | 4/2009 | Cuevas et al. |
| 2009/0101531 A1 | 4/2009 | Nordholm et al. |
| 2009/0112171 A1 | 4/2009 | Ng et al. |
| 2009/0131917 A1 | 5/2009 | Kavanagh et al. |
| 2009/0137985 A1 | 5/2009 | Tanghoej et al. |
| 2009/0137986 A1 | 5/2009 | Golden et al. |
| 2009/0149837 A1 | 6/2009 | Tanghoj et al. |
| 2009/0156882 A1 | 6/2009 | Chi Sing et al. |
| 2009/0163884 A1 | 6/2009 | Kull-Osterlin et al. |
| 2009/0200187 A1 | 8/2009 | Nestenborg et al. |
| 2009/0208368 A1 | 8/2009 | Waldrep et al. |
| 2009/0221992 A1 | 9/2009 | Hannon et al. |
| 2009/0299334 A1 | 12/2009 | Nishtala et al. |
| 2009/0314795 A1 | 12/2009 | Rapko et al. |
| 2009/0318900 A1 | 12/2009 | Tanghoj et al. |
| 2010/0010086 A1 | 1/2010 | Ash et al. |
| 2010/0030197 A1 | 2/2010 | House |
| 2010/0036363 A1 | 2/2010 | Watanabe et al. |
| 2010/0047123 A1 | 2/2010 | Solomon et al. |
| 2010/0086580 A1 | 4/2010 | Nyman et al. |
| 2010/0133172 A1 | 6/2010 | Song et al. |
| 2010/0152686 A1 | 6/2010 | Ryder et al. |
| 2010/0155268 A1 | 6/2010 | Murray et al. |
| 2010/0198195 A1 | 8/2010 | Nishtala et al. |
| 2010/0228233 A1 | 9/2010 | Kahn |
| 2010/0256576 A1 | 10/2010 | Aggarwal et al. |
| 2010/0258568 A1 | 10/2010 | Frederiksen et al. |
| 2010/0263327 A1 | 10/2010 | Murray et al. |
| 2010/0324540 A1 | 12/2010 | Paulen et al. |
| 2011/0028943 A1 | 2/2011 | Lawson et al. |
| 2011/0056852 A1 | 3/2011 | Frojd |
| 2011/0059874 A1 | 3/2011 | Rooijmans et al. |
| 2011/0060317 A1 | 3/2011 | Frojd |
| 2011/0114520 A1 | 5/2011 | Matthison-Hansen |
| 2011/0127186 A1 | 6/2011 | Enns et al. |
| 2011/0137243 A1 | 6/2011 | Hossainy et al. |
| 2011/0137296 A1 | 6/2011 | Tanghoj |
| 2011/0144579 A1 | 6/2011 | Elton |
| 2011/0147238 A1 | 6/2011 | Tanghoej et al. |
| 2011/0152843 A1 | 6/2011 | Wedlin et al. |
| 2011/0160704 A1 | 6/2011 | Park |
| 2011/0178507 A1 | 7/2011 | Bracken et al. |
| 2011/0184386 A1 | 7/2011 | House |
| 2011/0213025 A1 | 9/2011 | Finch, Jr. |
| 2011/0224653 A1 | 9/2011 | Torstensen |
| 2011/0284409 A1 | 11/2011 | Murray et al. |
| 2011/0295239 A1 | 12/2011 | Gustavsson |
| 2012/0037525 A1* | 2/2012 | Peck .................... A61L 2/206 |
| | | 206/363 |
| 2012/0168324 A1 | 7/2012 | Carleo |
| 2012/0179102 A1 | 7/2012 | Blanchard et al. |
| 2012/0179144 A1 | 7/2012 | Carleo |
| 2012/0193255 A1 | 8/2012 | Lareau et al. |
| 2012/0219742 A1 | 8/2012 | Gravesen et al. |
| 2012/0228165 A1 | 9/2012 | Murray et al. |
| 2012/0239005 A1 | 9/2012 | Conway et al. |

(56) References Cited

U.S. PATENT DOCUMENTS

| 2012/0271101 A1 | 10/2012 | Tan |
| 2012/0284991 A1 | 11/2012 | Kusz et al. |
| 2012/0308805 A1 | 12/2012 | Sella |
| 2012/0310210 A1 | 12/2012 | Campbell et al. |
| 2012/0316515 A1 | 12/2012 | Terry |
| 2012/0330255 A1 | 12/2012 | Carlin |
| 2013/0006226 A1 | 1/2013 | Hong et al. |
| 2013/0037306 A1 | 2/2013 | Kim |
| 2013/0048516 A1 | 2/2013 | Nishtala et al. |
| 2013/0077899 A1 | 3/2013 | Odabashian et al. |
| 2013/0085469 A1 | 4/2013 | Polaschegg |
| 2013/0131647 A1 | 5/2013 | Nielsen |
| 2013/0138083 A1 | 5/2013 | Tennican |
| 2013/0138088 A1 | 5/2013 | Nielsen |
| 2013/0146599 A1 | 6/2013 | Murray et al. |
| 2013/0153446 A1 | 6/2013 | Utas et al. |
| 2013/0161208 A1 | 6/2013 | Gustavsson |
| 2013/0161227 A1 | 6/2013 | Gustavsson |
| 2013/0186778 A1 | 7/2013 | Terry |
| 2013/0218136 A1 | 8/2013 | Tanghoej et al. |
| 2013/0231641 A1 | 9/2013 | Gustavsson |
| 2013/0253426 A1 | 9/2013 | Campbell et al. |
| 2013/0261608 A1 | 10/2013 | Tanghoj |
| 2013/0264227 A1 | 10/2013 | Frojd |
| 2013/0289537 A1 | 10/2013 | Schertiger et al. |
| 2014/0066904 A1 | 3/2014 | Young |
| 2014/0066905 A1 | 3/2014 | Young |
| 2014/0193474 A1 | 7/2014 | Babcock et al. |
| 2014/0194857 A1 | 7/2014 | Eilat |
| 2014/0224678 A1 | 8/2014 | Schertiger et al. |
| 2014/0262859 A1 | 9/2014 | Knapp et al. |
| 2014/0271351 A1 | 9/2014 | Nielsen et al. |
| 2014/0271400 A1 | 9/2014 | Cheng et al. |
| 2014/0287172 A1 | 9/2014 | Finley et al. |
| 2015/0001107 A1 | 1/2015 | Gustavsson |
| 2015/0018962 A1 | 1/2015 | Matsumoto et al. |
| 2015/0051587 A1 | 2/2015 | Rolsted et al. |
| 2015/0068927 A1 | 3/2015 | McBurney et al. |
| 2015/0105756 A1 | 4/2015 | O'Brien et al. |
| 2015/0126975 A1 | 5/2015 | Wuthier |
| 2015/0132468 A1 | 5/2015 | Cage et al. |
| 2015/0133898 A1 | 5/2015 | Murray et al. |
| 2015/0202405 A1 | 7/2015 | Schertiger et al. |
| 2015/0231377 A1 | 8/2015 | Tierney et al. |
| 2015/0238726 A1 | 8/2015 | Terry |
| 2015/0258305 A1 | 9/2015 | Dye |
| 2015/0265801 A1 | 9/2015 | Rostami |
| 2015/0273116 A1 | 10/2015 | Knapp et al. |
| 2015/0273183 A1 | 10/2015 | Foley et al. |
| 2015/0297861 A1 | 10/2015 | Passalaqua et al. |
| 2015/0297862 A1 | 10/2015 | Sadik et al. |
| 2015/0306342 A1 | 10/2015 | Rostami et al. |
| 2015/0314103 A1 | 11/2015 | Hannon et al. |
| 2015/0335823 A1 | 11/2015 | Weikart et al. |
| 2015/0335854 A1 | 11/2015 | Dvarsater et al. |
| 2015/0335856 A1 | 11/2015 | Utas et al. |
| 2015/0335872 A1 | 11/2015 | Yang et al. |
| 2015/0343171 A1 | 12/2015 | Hannon |
| 2015/0352324 A1 | 12/2015 | Palmer |
| 2015/0359996 A1 | 12/2015 | Arora et al. |
| 2016/0001037 A1 | 1/2016 | Hong et al. |
| 2016/0038652 A1 | 2/2016 | Gilman |
| 2016/0038713 A1 | 2/2016 | Kearns et al. |
| 2016/0120688 A1 | 5/2016 | Lee |
| 2016/0166822 A1 | 6/2016 | Dodson et al. |
| 2016/0175488 A1 | 6/2016 | Klein et al. |
| 2016/0184551 A1 | 6/2016 | Nyman et al. |
| 2016/0193447 A1 | 7/2016 | Matthiassen |
| 2016/0220784 A1 | 8/2016 | Palmer |
| 2016/0317715 A1 | 11/2016 | Rostami et al. |
| 2016/0325088 A1 | 11/2016 | Nordquist et al. |
| 2016/0325089 A1 | 11/2016 | Burkholz |
| 2017/0173300 A1 | 6/2017 | Hannon et al. |
| 2017/0217658 A1 | 8/2017 | Whitehurst |
| 2017/0296704 A1 | 10/2017 | Knapp et al. |
| 2017/0326334 A1 | 11/2017 | Terry |
| 2018/0021481 A1 | 1/2018 | Yin et al. |
| 2018/0050173 A1 | 2/2018 | Kearns |
| 2018/0071486 A1 | 3/2018 | O'Flynn |
| 2018/0104444 A1 | 4/2018 | Yin et al. |
| 2018/0110961 A1 | 4/2018 | Steindahl et al. |
| 2018/0163152 A1 | 6/2018 | Luo et al. |
| 2018/0169377 A1 | 6/2018 | Hickmott et al. |
| 2019/0047766 A1 | 2/2019 | Brooks et al. |
| 2019/0083746 A1 | 3/2019 | Murray et al. |
| 2019/0105462 A1 | 4/2019 | Schertiger |
| 2019/0110879 A1 | 4/2019 | Camp et al. |
| 2019/0126004 A1 | 5/2019 | O'Brien et al. |
| 2019/0151605 A1 | 5/2019 | McMenamin et al. |
| 2019/0151610 A1 | 5/2019 | Fletter |
| 2019/0216985 A1 | 7/2019 | Mcburney et al. |
| 2019/0255280 A1 | 8/2019 | Palmer |
| 2019/0321593 A1 | 10/2019 | Crawford |
| 2019/0358435 A1 | 11/2019 | Andersin et al. |
| 2019/0381272 A1 | 12/2019 | Terry |
| 2020/0001043 A1 | 1/2020 | Heneghan et al. |
| 2020/0016380 A1 | 1/2020 | Murray et al. |
| 2020/0031550 A1 | 1/2020 | Douglas et al. |
| 2020/0115102 A1 | 4/2020 | Hawry |
| 2020/0155261 A1 | 5/2020 | O'Flynn et al. |
| 2020/0155794 A1 | 5/2020 | Ziebol |
| 2020/0155796 A1 | 5/2020 | Hannon et al. |
| 2020/0171218 A1 | 6/2020 | Dong et al. |
| 2020/0179647 A1 | 6/2020 | Conway et al. |
| 2020/0188631 A1 | 6/2020 | Hannon et al. |
| 2020/0222659 A1 | 7/2020 | Schertiger et al. |
| 2020/0230349 A1 | 7/2020 | McMenamin et al. |
| 2020/0238048 A1 | 7/2020 | Palmer |
| 2020/0246594 A1 | 8/2020 | Miller |
| 2020/0281751 A1 | 9/2020 | Schreck et al. |
| 2020/0282177 A1 | 9/2020 | Farrell |
| 2020/0345977 A1 | 11/2020 | Hickmott et al. |
| 2020/0361076 A1 | 11/2020 | Richart |
| 2020/0383822 A1 | 12/2020 | Palmer |
| 2020/0391005 A1 | 12/2020 | Murray et al. |
| 2020/0398023 A1 | 12/2020 | Conway et al. |
| 2020/0398024 A1 | 12/2020 | Fletter et al. |
| 2021/0008361 A1 | 1/2021 | Aronson |
| 2021/0100979 A1 | 4/2021 | Donnelly et al. |
| 2021/0113808 A1 | 4/2021 | Yin et al. |
| 2021/0187238 A1 | 6/2021 | O'Brien et al. |
| 2021/0212808 A1 | 7/2021 | Wu et al. |
| 2021/0283367 A1 | 9/2021 | Peters |
| 2021/0290894 A1 | 9/2021 | Palmer |
| 2021/0290895 A1 | 9/2021 | Nielsen et al. |
| 2021/0402135 A1 | 12/2021 | McMenamin et al. |
| 2022/0023585 A1 | 1/2022 | Schertiger et al. |
| 2022/0054295 A1 | 2/2022 | Becker |
| 2022/0112018 A1 | 4/2022 | Montano et al. |
| 2022/0117850 A1 | 4/2022 | Romeo et al. |
| 2022/0142810 A1 | 5/2022 | Whittaker |
| 2022/0241549 A1 | 8/2022 | Murray et al. |
| 2022/0273837 A1 | 9/2022 | Paul et al. |
| 2022/0362536 A1 | 11/2022 | Nguyen et al. |
| 2023/0058911 A1 | 2/2023 | Nabors et al. |
| 2023/0072221 A1 | 3/2023 | Donnelly et al. |
| 2023/0073264 A1 | 3/2023 | Kandrac et al. |
| 2023/0075906 A1 | 3/2023 | Piashevich et al. |
| 2023/0077075 A1 | 3/2023 | Kandrac et al. |
| 2023/0166073 A1 | 6/2023 | Radmer |
| 2023/0293848 A1 | 9/2023 | Legaspi et al. |
| 2023/0293849 A1 | 9/2023 | Hughett, Sr. et al. |
| 2023/0364379 A1 | 11/2023 | Hughett, Sr. et al. |
| 2024/0269426 A1 | 8/2024 | Siddiqui |
| 2024/0325685 A1 | 10/2024 | Daw et al. |
| 2024/0342332 A1 | 10/2024 | Paras |
| 2025/0082897 A1 | 3/2025 | Pfleger |
| 2025/0114231 A1 | 4/2025 | Legaspi et al. |
| 2025/0288774 A1 | 9/2025 | Kulkarni et al. |

(56)  References Cited

U.S. PATENT DOCUMENTS

| | | | |
|---|---|---|---|
| 2025/0289618 A1 | 9/2025 | Simonsen et al. | |
| 2025/0325785 A1 | 10/2025 | Kulkarni et al. | |

FOREIGN PATENT DOCUMENTS

| | | | |
|---|---|---|---|
| AU | 2022354188 A1 | 3/2024 | |
| BR | PI0803737 A2 | 1/2010 | |
| CA | 763930 A | 7/1967 | |
| CA | 2770300 A1 | 2/2011 | |
| CA | 2769026 C | 4/2015 | |
| CA | 3083014 A1 | 5/2019 | |
| CN | 1106744 A | 8/1995 | |
| CN | 2532840 Y | 1/2003 | |
| CN | 2907580 Y | 6/2007 | |
| CN | 101035573 A | 9/2007 | |
| CN | 101365501 A | 2/2009 | |
| CN | 102939127 A | 2/2013 | |
| CN | 102939129 A | 2/2013 | |
| CN | 102973986 A | 3/2013 | |
| CN | 102973987 A | 3/2013 | |
| CN | 107088243 A | 8/2017 | |
| CN | 111870742 A | 11/2020 | |
| CN | 217015042 U | 7/2022 | |
| CN | 116056746 A | 5/2023 | |
| DE | 352014 C | 4/1922 | |
| DE | 1913976 U | 4/1965 | |
| DE | 4135502 C1 | 2/1993 | |
| DE | 4303899 A1 | 8/1994 | |
| DE | 19826746 C1 | 11/1999 | |
| DE | 10038521 A1 | 2/2002 | |
| DE | 10213411 A1 | 10/2003 | |
| DE | 10259002 A1 | 10/2003 | |
| DE | 10334372 A1 | 2/2005 | |
| DE | 202005009946 U1 | 9/2005 | |
| DE | 202005009947 U1 | 9/2005 | |
| DE | 102007018275 A1 | 3/2008 | |
| DE | 102009025347 A1 | 12/2010 | |
| DE | 202012000538 U1 | 3/2012 | |
| DE | 202011107059 U1 | 1/2013 | |
| DE | 202013002466 U1 | 3/2013 | |
| DE | 102011085864 A1 | 5/2013 | |
| DE | 102012000844 A1 | 7/2013 | |
| DE | 102016120294 A1 | 4/2018 | |
| DE | 112018000170 T5 | 10/2019 | |
| EP | 0055023 A2 | 6/1982 | |
| EP | 0182409 A1 | 5/1986 | |
| EP | 0184629 A2 | 6/1986 | |
| EP | 0187846 A1 | 7/1986 | |
| EP | 0193406 A2 | 9/1986 | |
| EP | 0218203 A1 | 4/1987 | |
| EP | 0236458 A1 | 9/1987 | |
| EP | 247559 A1 | 12/1987 | |
| EP | 0252918 A1 | 1/1988 | |
| EP | 0298634 A1 | 1/1989 | |
| EP | 0303487 A2 | 2/1989 | |
| EP | 0335564 A1 | 10/1989 | |
| EP | 0352043 A1 | 1/1990 | |
| EP | 0390720 A1 | 10/1990 | |
| EP | 0407218 A1 | 1/1991 | |
| EP | 0217771 B1 | 12/1991 | |
| EP | 0471553 A1 | 2/1992 | |
| EP | 0479935 A1 | 4/1992 | |
| EP | 0528965 A1 | 3/1993 | |
| EP | 0553960 A1 | 8/1993 | |
| EP | 0590104 A1 | 4/1994 | |
| EP | 0598191 A1 | 5/1994 | |
| EP | 0663196 A1 | 7/1995 | |
| EP | 0677299 A1 | 10/1995 | |
| EP | 0680895 A1 | 11/1995 | |
| EP | 0685179 A1 | 12/1995 | |
| EP | 0699086 A1 | 3/1996 | |
| EP | 0767639 A1 | 4/1997 | |
| EP | 0768069 A1 | 4/1997 | |
| EP | 0795339 A1 | 9/1997 | |
| EP | 0815037 A1 | 1/1998 | |
| EP | 0909249 A1 | 4/1999 | |
| EP | 0923398 A1 | 6/1999 | |
| EP | 0935478 A1 | 8/1999 | |
| EP | 0977610 A2 | 2/2000 | |
| EP | 1018323 A1 | 7/2000 | |
| EP | 1023882 A1 | 8/2000 | |
| EP | 1047360 A1 | 11/2000 | |
| EP | 1115450 A1 | 7/2001 | |
| EP | 1131022 A1 | 9/2001 | |
| EP | 1175355 A1 | 1/2002 | |
| EP | 1237615 A1 | 9/2002 | |
| EP | 1245205 A2 | 10/2002 | |
| EP | 0959930 B1 | 12/2002 | |
| EP | 1308146 A1 | 5/2003 | |
| EP | 1321163 A1 | 6/2003 | |
| EP | 1347723 A1 | 10/2003 | |
| EP | 1406690 A2 | 4/2004 | |
| EP | 1409060 A2 | 4/2004 | |
| EP | 1090656 B1 | 5/2004 | |
| EP | 1420846 A1 | 5/2004 | |
| EP | 1420847 A2 | 5/2004 | |
| EP | 1427467 A2 | 6/2004 | |
| EP | 1485158 A2 | 12/2004 | |
| EP | 1498151 A2 | 1/2005 | |
| EP | 1567219 A1 | 8/2005 | |
| EP | 1578308 A1 | 9/2005 | |
| EP | 1145729 B1 | 11/2005 | |
| EP | 1606196 A2 | 12/2005 | |
| EP | 1615690 A1 | 1/2006 | |
| EP | 1629799 A1 | 3/2006 | |
| EP | 1629860 | 3/2006 | |
| EP | 1641510 A1 | 4/2006 | |
| EP | 1642610 | 4/2006 | |
| EP | 1642611 | 4/2006 | |
| EP | 1695678 A1 | 8/2006 | |
| EP | 1357868 B1 | 9/2006 | |
| EP | 1723980 A2 | 11/2006 | |
| EP | 1744803 A2 | 1/2007 | |
| EP | 1757251 A2 | 2/2007 | |
| EP | 1788990 A1 | 5/2007 | |
| EP | 1793938 A1 | 6/2007 | |
| EP | 1799163 A1 | 6/2007 | |
| EP | 1824534 A2 | 8/2007 | |
| EP | 1824549 A2 | 8/2007 | |
| EP | 1858575 A1 | 11/2007 | |
| EP | 1904003 A2 | 4/2008 | |
| EP | 1948279 A1 | 7/2008 | |
| EP | 1955683 A1 | 8/2008 | |
| EP | 2060296 A1 | 5/2009 | |
| EP | 2106821 A1 | 10/2009 | |
| EP | 2275058 A1 | 1/2011 | |
| EP | 2292293 A1 | 3/2011 | |
| EP | 2292294 A1 | 3/2011 | |
| EP | 2308542 A1 | 4/2011 | |
| EP | 2423125 A1 | 2/2012 | |
| EP | 2423126 A1 | 2/2012 | |
| EP | 2423127 A1 | 2/2012 | |
| EP | 2450076 A1 | 5/2012 | |
| EP | 2459264 A1 | 6/2012 | |
| EP | 2464411 A1 | 6/2012 | |
| EP | 2468347 A1 | 6/2012 | |
| EP | 2500056 A2 | 9/2012 | |
| EP | 1786501 B1 | 11/2012 | |
| EP | 2542291 A1 | 1/2013 | |
| EP | 1578468 B1 | 4/2013 | |
| EP | 2574354 A1 | 4/2013 | |
| EP | 2424470 B1 | 8/2013 | |
| EP | 2504054 B1 | 9/2013 | |
| EP | 2644224 A2 | 10/2013 | |
| EP | 2644224 A3 | 3/2014 | |
| EP | 1962937 B1 | 8/2014 | |
| EP | 2774648 A1 | 9/2014 | |
| EP | 2515985 B1 | 12/2014 | |
| EP | 2686054 B1 | 12/2014 | |
| EP | 2908897 A1 | 8/2015 | |
| EP | 2898918 A3 | 9/2015 | |
| EP | 2914222 A1 | 9/2015 | |
| EP | 2967968 A1 | 1/2016 | |
| EP | 1852139 B1 | 5/2016 | |

(56) References Cited

FOREIGN PATENT DOCUMENTS

| | | | |
|----|----|----|----|
| EP | 2515988 | B1 | 7/2016 |
| EP | 2777747 | B1 | 5/2017 |
| EP | 3199130 | A1 | 8/2017 |
| EP | 3231471 | A1 | 10/2017 |
| EP | 3078393 | B1 | 11/2017 |
| EP | 3272385 | A1 | 1/2018 |
| EP | 3222316 | B1 | 5/2018 |
| EP | 3352831 | A1 | 8/2018 |
| EP | 2644224 | B1 | 11/2018 |
| EP | 2782629 | B1 | 4/2019 |
| EP | 3313494 | B1 | 5/2019 |
| EP | 3478353 | A1 | 5/2019 |
| EP | 2826514 | B1 | 6/2019 |
| EP | 3490654 | A1 | 6/2019 |
| EP | 2946803 | B1 | 7/2019 |
| EP | 3551103 | A1 | 10/2019 |
| EP | 3566739 | A1 | 11/2019 |
| EP | 3570925 | A1 | 11/2019 |
| EP | 3092024 | B1 | 12/2019 |
| EP | 3583972 | A2 | 12/2019 |
| EP | 3388103 | B1 | 1/2020 |
| EP | 3590573 | A1 | 1/2020 |
| EP | 3079752 | B1 | 4/2020 |
| EP | 3100758 | B1 | 4/2020 |
| EP | 2826515 | B1 | 5/2020 |
| EP | 3079748 | B1 | 5/2020 |
| EP | 3651844 | A1 | 5/2020 |
| EP | 2651485 | B1 | 6/2020 |
| EP | 3038690 | B1 | 7/2020 |
| EP | 3119464 | B1 | 9/2020 |
| EP | 3132823 | B1 | 9/2020 |
| EP | 3299056 | B1 | 9/2020 |
| EP | 3701993 | A1 | 9/2020 |
| EP | 3709940 | A1 | 9/2020 |
| EP | 3710095 | A1 | 9/2020 |
| EP | 3711806 | A1 | 9/2020 |
| EP | 3711807 | A1 | 9/2020 |
| EP | 3711808 | A1 | 9/2020 |
| EP | 3713632 | A2 | 9/2020 |
| EP | 3392167 | B1 | 10/2020 |
| EP | 2468346 | B1 | 11/2020 |
| EP | 3077031 | B1 | 11/2020 |
| EP | 3738640 | A1 | 11/2020 |
| EP | 3769803 | A2 | 1/2021 |
| EP | 2995268 | B1 | 3/2021 |
| EP | 3793627 | A1 | 3/2021 |
| EP | 2968833 | B1 | 5/2021 |
| EP | 3952973 | A1 | 2/2022 |
| EP | 3082929 | B1 | 3/2022 |
| EP | 3310421 | B1 | 3/2022 |
| EP | 3725355 | B1 | 5/2022 |
| EP | 2688629 | B1 | 12/2022 |
| ES | 2645658 | B1 | 10/2018 |
| FR | 1558162 | A | 2/1969 |
| FR | 96086 | E | 5/1972 |
| FR | 2127704 | A5 | 10/1972 |
| FR | 2351634 | A1 | 12/1977 |
| FR | 2731345 | A1 | 9/1996 |
| FR | 2794638 | A1 | 12/2000 |
| FR | 2855399 | A1 | 12/2004 |
| FR | 3042716 | B1 | 10/2021 |
| GB | 322426 | A | 12/1929 |
| GB | 1131865 | A | 10/1968 |
| GB | 2007507 | A | 5/1979 |
| GB | 2106784 | A | 4/1983 |
| GB | 2150938 | A | 7/1985 |
| GB | 2187670 | A | 9/1987 |
| GB | 2231801 | A | 11/1990 |
| GB | 2239804 | A | 7/1991 |
| GB | 2319507 | | 5/1998 |
| GB | 2284764 | B | 8/1998 |
| GB | 2427362 | B | 9/2008 |
| GB | 2462267 | A | 2/2010 |
| GB | 2469824 | B | 8/2011 |
| GB | 2532459 | B | 12/2016 |
| GB | 2565585 | A | 2/2019 |
| GB | 2561843 | B | 9/2021 |
| JP | S5512265 | B2 | 3/1980 |
| JP | S59218157 | A | 12/1984 |
| JP | S59228856 | A | 12/1984 |
| JP | H0218157 | A | 1/1990 |
| JP | H09206370 | A | 8/1997 |
| JP | H10151094 | A | 6/1998 |
| JP | H10277144 | A | 10/1998 |
| JP | 2001500414 | A | 1/2001 |
| JP | 200150329 | A | 2/2001 |
| JP | 2002530148 | A | 9/2002 |
| JP | 2002282275 | A | 10/2002 |
| JP | 2002543885 | A | 12/2002 |
| JP | 2007501656 | A | 2/2007 |
| JP | 2007167158 | A | 7/2007 |
| JP | 200851549 | A | 3/2008 |
| JP | 2008508077 | A | 3/2008 |
| JP | 2008526377 | A | 7/2008 |
| JP | 2009125583 | A | 6/2009 |
| JP | 2010538106 | A | 12/2010 |
| JP | 2011510110 | A | 3/2011 |
| JP | 2013500125 | A | 1/2013 |
| JP | 2013515572 | | 5/2013 |
| KR | 1020160035437 | A | 3/2016 |
| RU | 2009105497 | A | 8/2010 |
| WO | 1984001102 | A1 | 3/1984 |
| WO | 198401296 | A1 | 4/1984 |
| WO | 1986000816 | A1 | 2/1986 |
| WO | 1986006284 | A1 | 11/1986 |
| WO | 1987001582 | A1 | 3/1987 |
| WO | 1989003232 | A1 | 4/1989 |
| WO | 1989009626 | A1 | 10/1989 |
| WO | 1990004431 | A1 | 5/1990 |
| WO | 1991005577 | A1 | 5/1991 |
| WO | 1991010466 | A1 | 7/1991 |
| WO | 1991017728 | A1 | 11/1991 |
| WO | 9208426 | A1 | 5/1992 |
| WO | 1992008426 | A1 | 5/1992 |
| WO | 1992010220 | A1 | 6/1992 |
| WO | 1992011826 | A1 | 7/1992 |
| WO | 1992019192 | A1 | 11/1992 |
| WO | 1993000054 | A1 | 1/1993 |
| WO | 9311821 | A1 | 6/1993 |
| WO | 9314806 | A1 | 8/1993 |
| WO | 1994006377 | A1 | 3/1994 |
| WO | 1994016747 | A1 | 8/1994 |
| WO | 1994026215 | A1 | 11/1994 |
| WO | 1995008968 | A1 | 4/1995 |
| WO | 1995009667 | A1 | 4/1995 |
| WO | 1995017862 | A1 | 7/1995 |
| WO | 1995034253 | A1 | 12/1995 |
| WO | 1996000541 | A1 | 1/1996 |
| WO | 1996004119 | A1 | 2/1996 |
| WO | 9607447 | A1 | 3/1996 |
| WO | 1996019254 | A1 | 6/1996 |
| WO | 1996026688 | A1 | 9/1996 |
| WO | 1996030277 | A1 | 10/1996 |
| WO | 1996034587 | A1 | 11/1996 |
| WO | 9641653 | A1 | 12/1996 |
| WO | 1996038192 | A1 | 12/1996 |
| WO | 1996039096 | A1 | 12/1996 |
| WO | 1997025947 | A1 | 7/1997 |
| WO | 1997026937 | A1 | 7/1997 |
| WO | 1997041811 | A1 | 11/1997 |
| WO | 1998006642 | A1 | 2/1998 |
| WO | 1998011932 | | 3/1998 |
| WO | 1998019729 | | 5/1998 |
| WO | 9846176 | A1 | 10/1998 |
| WO | 1999007313 | A1 | 2/1999 |
| WO | 1999030761 | A1 | 6/1999 |
| WO | 1999036609 | A1 | 7/1999 |
| WO | 2000016843 | | 3/2000 |
| WO | 2000025848 | A2 | 5/2000 |
| WO | 0030696 | A1 | 6/2000 |
| WO | 2000030575 | A1 | 6/2000 |
| WO | 2000047494 | A1 | 8/2000 |
| WO | 2001043807 | A1 | 6/2001 |
| WO | 2001052763 | A1 | 7/2001 |

(56) References Cited

FOREIGN PATENT DOCUMENTS

| | | | |
|---|---|---|---|
| WO | 2001093935 | A1 | 12/2001 |
| WO | 2002036192 | A1 | 5/2002 |
| WO | 2002053070 | A1 | 7/2002 |
| WO | 2002060361 | A2 | 8/2002 |
| WO | 03008028 | A2 | 1/2003 |
| WO | 03008029 | A2 | 1/2003 |
| WO | 2003002177 | | 1/2003 |
| WO | 2003002178 | A2 | 1/2003 |
| WO | 2003022333 | A1 | 3/2003 |
| WO | 2003064279 | A1 | 8/2003 |
| WO | 03092779 | A1 | 11/2003 |
| WO | 03093357 | A1 | 11/2003 |
| WO | 2004004611 | A1 | 1/2004 |
| WO | 2004004796 | A1 | 1/2004 |
| WO | 2004030722 | A2 | 4/2004 |
| WO | 2004032992 | A2 | 4/2004 |
| WO | 2004045696 | A1 | 6/2004 |
| WO | 2004050155 | A1 | 6/2004 |
| WO | 2004052440 | A1 | 6/2004 |
| WO | 2004056290 | A1 | 7/2004 |
| WO | 2004056414 | A1 | 7/2004 |
| WO | 2004056909 | A1 | 7/2004 |
| WO | 2004075944 | A2 | 9/2004 |
| WO | 2004089454 | A1 | 10/2004 |
| WO | 2005004964 | A1 | 1/2005 |
| WO | 2005014055 | A2 | 2/2005 |
| WO | 2005061035 | A1 | 7/2005 |
| WO | 2005092418 | A1 | 10/2005 |
| WO | 2006005349 | A2 | 1/2006 |
| WO | 2006009509 | A1 | 1/2006 |
| WO | 2006009596 | A1 | 1/2006 |
| WO | 2006017439 | A2 | 2/2006 |
| WO | 2006021590 | A1 | 3/2006 |
| WO | 2006027349 | A1 | 3/2006 |
| WO | 2006033234 | A1 | 3/2006 |
| WO | 2006037321 | A1 | 4/2006 |
| WO | 2006097109 | A2 | 9/2006 |
| WO | 2006110695 | A2 | 10/2006 |
| WO | 2006112782 | A1 | 10/2006 |
| WO | 2006130776 | A2 | 12/2006 |
| WO | 2007001526 | A2 | 1/2007 |
| WO | 2007038988 | A1 | 4/2007 |
| WO | 2007083033 | A2 | 7/2007 |
| WO | 2008089770 | A1 | 7/2008 |
| WO | 2008104573 | A2 | 9/2008 |
| WO | 2008104603 | A1 | 9/2008 |
| WO | 2008138351 | A1 | 11/2008 |
| WO | 2008138352 | A1 | 11/2008 |
| WO | 2008151074 | A1 | 12/2008 |
| WO | 2009000277 | A1 | 12/2008 |
| WO | 2009012336 | A1 | 1/2009 |
| WO | 2009017541 | A1 | 2/2009 |
| WO | 2007050685 | A3 | 4/2009 |
| WO | 2009043872 | A1 | 4/2009 |
| WO | 2009068043 | A2 | 6/2009 |
| WO | 2009080265 | A1 | 7/2009 |
| WO | 2009108243 | A1 | 9/2009 |
| WO | 2010006620 | A1 | 1/2010 |
| WO | 2010041084 | A1 | 4/2010 |
| WO | 2010054659 | A1 | 5/2010 |
| WO | 2010054666 | A1 | 5/2010 |
| WO | 2010129362 | A1 | 11/2010 |
| WO | 2010130261 | A1 | 11/2010 |
| WO | 2010149174 | A1 | 12/2010 |
| WO | 2010149175 | A1 | 12/2010 |
| WO | 2010151682 | A2 | 12/2010 |
| WO | 2011011023 | A1 | 1/2011 |
| WO | 2011014201 | A1 | 2/2011 |
| WO | 2011019359 | A1 | 2/2011 |
| WO | 2011026929 | A1 | 3/2011 |
| WO | 2011026930 | A1 | 3/2011 |
| WO | 2011063816 | A1 | 6/2011 |
| WO | 2011073403 | A1 | 6/2011 |
| WO | 2011076211 | A1 | 6/2011 |
| WO | 2011079129 | A1 | 6/2011 |
| WO | 2011109393 | A1 | 9/2011 |
| WO | 2012016570 | A2 | 2/2012 |
| WO | 2012016571 | A2 | 2/2012 |
| WO | 2012079590 | A1 | 6/2012 |
| WO | 2012085124 | A1 | 6/2012 |
| WO | 2012126474 | A1 | 9/2012 |
| WO | 2012134804 | A1 | 10/2012 |
| WO | 2012139214 | A1 | 10/2012 |
| WO | 2013010745 | A1 | 1/2013 |
| WO | 2013029621 | A1 | 3/2013 |
| WO | 2013075725 | A1 | 5/2013 |
| WO | 2014062225 | A1 | 4/2014 |
| WO | 2014081859 | A1 | 5/2014 |
| WO | 2014142917 | A1 | 9/2014 |
| WO | 2014142923 | A1 | 9/2014 |
| WO | 2014165046 | A1 | 10/2014 |
| WO | 15069843 | A2 | 5/2015 |
| WO | 2015075841 | A1 | 5/2015 |
| WO | 15090338 | A1 | 6/2015 |
| WO | 2015089189 | A2 | 6/2015 |
| WO | 2015105942 | A1 | 7/2015 |
| WO | 15142506 | A1 | 9/2015 |
| WO | 2015184365 | A1 | 12/2015 |
| WO | 201603323 | A1 | 1/2016 |
| WO | 2016008493 | A1 | 1/2016 |
| WO | 2016116915 | A1 | 7/2016 |
| WO | 2016206701 | A1 | 12/2016 |
| WO | 2017185052 | A1 | 10/2017 |
| WO | 2018029279 | A1 | 2/2018 |
| WO | 2018059637 | A1 | 4/2018 |
| WO | 2018134748 | A1 | 7/2018 |
| WO | 2018150975 | A1 | 8/2018 |
| WO | 2018156589 | A2 | 8/2018 |
| WO | 2018219433 | A1 | 12/2018 |
| WO | 2019002066 | A2 | 1/2019 |
| WO | 2019014344 | A1 | 1/2019 |
| WO | 2019070984 | A1 | 4/2019 |
| WO | 2019083104 | A1 | 5/2019 |
| WO | 2019083839 | A1 | 5/2019 |
| WO | 2019099845 | A1 | 5/2019 |
| WO | 2019099975 | A2 | 5/2019 |
| WO | 2019113203 | A1 | 6/2019 |
| WO | 2019123004 | A1 | 6/2019 |
| WO | 2019123005 | A1 | 6/2019 |
| WO | 2019245679 | A1 | 12/2019 |
| WO | 2020006527 | A1 | 1/2020 |
| WO | 2020015804 | A1 | 1/2020 |
| WO | 2020106822 | A1 | 5/2020 |
| WO | 2020125908 | A1 | 6/2020 |
| WO | 2020223146 | A1 | 11/2020 |
| WO | 2020237286 | A1 | 12/2020 |
| WO | 2020251961 | A1 | 12/2020 |
| WO | 2020252003 | A1 | 12/2020 |
| WO | 2020263859 | A1 | 12/2020 |
| WO | 2021034487 | A1 | 2/2021 |
| WO | 2021041703 | A1 | 3/2021 |
| WO | 2021051158 | A1 | 3/2021 |
| WO | 2021077103 | A1 | 4/2021 |
| WO | 2021087099 | A1 | 5/2021 |
| WO | 2021092271 | A1 | 5/2021 |
| WO | 2021097519 | A1 | 5/2021 |
| WO | 2021108115 | A1 | 6/2021 |
| WO | 2021115840 | A1 | 6/2021 |
| WO | 2021127040 | A1 | 6/2021 |
| WO | 2021183718 | A1 | 9/2021 |
| WO | 2022031520 | A1 | 2/2022 |
| WO | 2022031550 | A1 | 2/2022 |
| WO | 2022056263 | A2 | 3/2022 |
| WO | 2022223978 | A1 | 10/2022 |
| WO | 2022223980 | A1 | 10/2022 |
| WO | 2022223983 | A1 | 10/2022 |
| WO | 2022223985 | A1 | 10/2022 |
| WO | 2022223987 | A1 | 10/2022 |
| WO | 2022260831 | A1 | 12/2022 |
| WO | 2023003682 | A1 | 1/2023 |
| WO | 2023055832 | A1 | 4/2023 |
| WO | 2023180707 | A1 | 9/2023 |
| WO | 2023211421 | A1 | 11/2023 |
| WO | 2024112323 | A1 | 5/2024 |

(56) References Cited

FOREIGN PATENT DOCUMENTS

| WO | 2024112324 A1 | 5/2024 |
| WO | 2024112325 A1 | 5/2024 |
| WO | 2024112799 A1 | 5/2024 |
| WO | 2024112805 A1 | 5/2024 |
| WO | 2025193963 A1 | 9/2025 |
| WO | 2025221562 A1 | 10/2025 |

OTHER PUBLICATIONS

"Tripartite Biocompatibility Guidance for Medical Devices," DSMA (Apr. 24, 1987).

AU 2014248744 filed Jul. 9, 2015 Examiner's Report dated Jul. 26, 2017.

BR PI 0506836-3 filed Jan. 18, 2005, Technical Report dated Jul. 28, 2015.

CA 2,769,026 filed Jan. 24, 2012 First Examination Report dated Nov. 4, 2013.

CN 201080058895.4 filed Jun. 21, 2012 First Office Action dated Feb. 27, 2014.

CN 201080058895.4 filed Jun. 21, 2012 Second Office Action dated Nov. 3, 2014.

CN 201080058895.4 filed Jun. 21, 2012 Third Office Action dated May 4, 2015.

CN 201480013064.3 filed Sep. 8, 2015 Office Action dated Jun. 29, 2017.

CN 201480013064.3 filed Sep. 8, 2015 Office Action dated Oct. 10, 2016.

EP 09848341.5 filed Feb. 27, 2012 extended European Search Report dated Apr. 4, 2013.

EP 09848341.5 filed Feb. 27, 2012 supplemental European Search Report dated Nov. 8, 2013.

EP 10840071.4 filed Jul. 4, 2012 Exam Report dated Apr. 29, 2014.

EP 10840071.4 filed Jul. 4, 2012 extended European Search Report dated Apr. 17, 2013.

EP 10840071.4 filed Jul. 4, 2012 Notice of Opposition dated Apr. 24, 2017.

EP 10840071.4 filed Jul. 4, 2012 Office Action dated Jul. 9, 2015.

EP 11751198.0 filed Sep. 28, 2012 Exam Report dated Feb. 7, 2014.

EP 11751198.0 filed Sep. 28, 2012 extended European search report dated Jul. 9, 2013.

EP 14779919.1 filed Sep. 10, 2015 Extended European Search Report dated Aug. 23, 2016.

EP 14779919.1 filed Sep. 10, 2015 Office Action dated Jul. 4, 2017.

EP 16171279.9 filed May 25, 2016 Extended European Search Report, dated Aug. 23, 2016.

EP 16171279.9 filed May 25, 2016 Intent to Grant, dated Jun. 13, 2017.

EP 17201044.9 filed Nov. 10, 2017 Extended European Search Report dated Jan. 18, 2018.

EP 17201044.9 filed Nov. 10, 2017 Office Action dated Jul. 4, 2019.

JP 2012-546157 filed Jun. 12, 2012 Decision of Rejection dated Aug. 21, 2015.

JP 2012-546157 filed Jun. 12, 2012 First Office Action dated Sep. 16, 2014.

JP 2015-243156 filed Dec. 14, 2015 Office Action dated Sep. 16, 2016.

JP 2016-501444 filed Sep. 11, 2015 Office Action dated Dec. 14, 2017.

Moore et al., "The Swelling of Cotton in Water: A Microscopical Study," Textile Research Journal, vol. 20, Issue 9 pp. 620-630, Sep. 1, 1950.

MX/a/2015/009904 filed Jul. 30, 2015 Office Action dated Jun. 29, 2018.

Newman et al. "Review of Intermittent Catheterization and Current Best Practices," Urological Nursing, vol. 31, No. 1 pp. 12-29, 48, Jan. 2011.

Norton, J.A. et al., Surgery: Basic Science and Clinical Evidence Springer, 2nd ed., 2008, p. 281.

PCT/US2006/041633 filed Oct. 25, 2006 International Preliminary Report on Patentability dated Mar. 24, 2009.

PCT/US2006/041633 filed Oct. 25, 2006 Search Report dated Aug. 12, 2008.

PCT/US2006/041633 filed Oct. 25, 2006 Written Opinion dated Aug. 12, 2008.

PCT/US2009/055389 filed Aug. 28, 2009 International Search Report dated Oct. 20, 2009.

PCT/US2009/055389 filed Aug. 28, 2009 Written Opinion dated Oct. 20, 2009.

PCT/US2009/055395 filed Aug. 28, 2009 International Preliminary Report on Patentability dated Jan. 31, 2012.

PCT/US2009/055395 filed Aug. 28, 2009 International Search Report dated Oct. 15, 2009.

PCT/US2009/055395 filed Aug. 28, 2009 Written Opinion dated Oct. 15, 2009.

PCT/US2010/061597 filed Dec. 21, 2010 International Preliminary Report on Patentability dated Jun. 26, 2012 and Written Opinion dated Feb. 28, 2011.

PCT/US2010/061597 filed Dec. 21, 2010 International Search Report dated Feb. 28, 2011.

PCT/US2011/026681 filed Mar. 1, 2011 International Preliminary Report on Patentability dated Sep. 4, 2012.

PCT/US2011/026681 filed Mar. 1, 2011 International Search Report dated Apr. 27, 2011.

PCT/US2011/026681 filed Mar. 1, 2011 Written Opinion dated Apr. 27, 2011.

PCT/US2014/024231 filed Mar. 12, 2014 International Search Report and Written Opinion dated Jul. 10, 2014.

PCT/US2021/043771 filed Jul. 29, 2021 International Search Report and Written Opinion dated Jan. 24, 2022.

PCT/US2021/044021 filed Jul. 30, 2021 International Search Report and Written Opinion dated Jan. 24, 2022.

PCT/US2021/049867 filed Sep. 10, 2021 International Search Report and Written Opinion dated Mar. 11, 2022.

PCT/US2022/029431 filed May 16, 2022 International Search Report and Written Opinion dated Sep. 15, 2022.

U.S. Appl. No. 15/669,697, filed Aug. 4, 2017 Notice of Allowance dated Mar. 1, 2019.

U.S. Appl. No. 16/453,809, filed Jun. 26, 2019 Notice of Allowance dated Apr. 14, 2020.

Wong, "Hydrogels, water-absorbing polymers" Catalyst, vol. 18, Issue 1, pp. 18-21, Sep. 2007.

PCT/US2022/050645 filed Nov. 21, 2022 International Search Report and Written Opinion dated Jun. 28, 2023.

PCT/US2022/050646 filed Nov. 21, 2022 International Search Report and Written Opinion dated May 30, 2023.

PCT/US2022/050648 filed Nov. 21, 2022 International Search Report and Written Opinion dated Jun. 16, 2023.

PCT/US2025/023972 filed Apr. 9, 2025 International Search Report and Written Opinion dated Sep. 18, 2025.

U.S. Appl. No. 17/796,611, filed Jul. 29, 2022 Final Office Action dated Sep. 24, 2025.

U.S. Appl. No. 18/019,464, filed Feb. 2, 2023 Non-Final Office Action dated Jul. 30, 2025.

U.S. Appl. No. 18/019,647, filed Feb. 3, 2023 Non-Final Office Action dated Jul. 31, 2025.

U.S. Appl. No. 18/025,875, filed Mar. 10, 2023 Non-Final Office Action dated Aug. 28, 2025.

U.S. Appl. No. 18/641,181, filed Apr. 19, 2024 Restriction Requirement dated Oct. 21, 2025.

Akzo Nobel, "Ethomeen C/25 technical data sheet" Mar. 10, 2009.

Amirkhai Il et al., "Nitric Oxide Complexes of Trimethylaluminium" Journal of Organometallic Chemistry, 149 (1978).

Angus "Chemie GmbHTechnical Data Sheet", AMP-95, TDS 10A (2000).

AU 2015306630 filed Feb. 2, 2017 Office Action dated Aug. 2, 2018.

BR1120170040301 filed Feb. 21, 2017 Office Action dated Aug. 20, 2019.

CN 20158004662.3 filed Feb. 24, 2017 Office Action dated Jul. 8, 2019.

(56)　　　　　References Cited

OTHER PUBLICATIONS

CN 20158004662.3 filed Feb. 24, 2017 Office Action dated Sep. 20, 2019.
EP 15836062.8 filed Feb. 17, 2017 Extended European Search Report dated Feb. 20, 2018.
EP 15836062.8 filed Feb. 17, 2017 Office Action dated Feb. 19, 2019.
Hollister, "Vapro intermittent catheter brochure" (2009).
Johnson et al. "Activities of a Nitrofurazone-Containing Urinary Catheter and a Silver Hydrogel Catheter against Multidrug-Resistant Bacteria Characteristic of Catheter-Associated Urinary Tract Infection" Antimicrobial Agents and Chemotherapy, Dec. 1999.
JP 2017-511223 filed Feb. 24, 2017 Office Action dated Jun. 4, 2019.
Lubrizol, "Neutralizing Carbopol®* and Pemulen™* Polymers in Aqueous and Hydroalcoholic Systems" Technical Data Sheet TDS-237 Edition: Sep. 16, 2009.
MX/a/2017/002457 filed Feb. 23, 2017 Office Action dated Sep. 4, 2019.
Newman "Intermittent Catheterization and Current Best Practices: Catheter Design and Types"; http://www.medscape.com/viewarticle/745908_8, last accessed May 31, 2013.
PCTUS2018054378 filed Oct. 4, 2018 International Preliminary Report on Patentability dated Jan. 2, 2019.
PCTUS2018054378 filed Oct. 4, 2018 International Search Report and Written opinion dated Jan. 2, 2019.
U.S. Appl. No. 15/506,723, filed Feb. 24, 2017 Final Office Action dated Dec. 9, 2019.
U.S. Appl. No. 15/506,723, filed Feb. 24, 2017 Non-Final Office Action dated Aug. 27, 2019.
U.S. Appl. No. 15/506,723, filed Feb. 24, 2017 Notice of Allowance dated Jul. 29, 2020.
U.S. Appl. No. 15/724,879, filed Oct. 4, 2017 Advisory Action dated Jan. 29, 2019.
U.S. Appl. No. 15/724,879, filed Oct. 4, 2017 Examiner's Answer dated Jul. 25, 2019.
U.S. Appl. No. 15/724,879, filed Oct. 4, 2017 Final Office Action dated Dec. 4, 2018.
U.S. Appl. No. 15/724,879, filed Oct. 4, 2017 Non-Final Office Action dated Jul. 19, 2018.
U.S. Appl. No. 15/724,879, filed Oct. 4, 2017 Notice of Allowance dated Aug. 14, 2020.
U.S. Appl. No. 15/724,879, filed Oct. 4, 2017 PTAB Decision on Appeal dated Jul. 1, 2020.
U.S. Appl. No. 15/724,879, filed Oct. 4, 2017 Restriction Requirement dated Mar. 7, 2018.
U.S. Appl. No. 17/114,275, filed Dec. 7, 2020 Final Office Action dated May 23, 2023.
U.S. Appl. No. 17/114,275, filed Dec. 7, 2020 Non-Final Office Action dated Jan. 31, 2023.
U.S. Appl. No. 17/114,275, filed Dec. 7, 2020 Notice of Allowance dated Aug. 9, 2023.
EP 24164460.8 filed Mar. 19, 2024 Extended European Search Report dated Jun. 19, 2024.
PCT/US2022/045084 filed Sep. 28, 2022 International Search Report and Written Opinion dated Jan. 3, 2023.
PCT/US2023/080761 filed Nov. 21, 2023 International Search Report and Written Opinion dated Apr. 9, 2024.
PCT/US2023/080769 filed Nov. 21, 2023 International Search Report and Written Opinion dated Mar. 15, 2024.
PCT/US2025/019799 filed Mar. 13, 2025 International Search Report and Written Opinion dated Jun. 4, 2025.
U.S. Appl. No. 18/019,464, filed Feb. 2, 2023 Restriction Requirement dated May 6, 2025.
U.S. Appl. No. 18/019,647, filed Feb. 3, 2023 Restriction Requirement dated May 8, 2025.
U.S. Appl. No. 18/025,875, filed Mar. 10, 2023 Restriction Requirement dated Jun. 4, 2025.

U.S. Appl. No. 18/604,394, filed Mar. 13, 2024 Non-Final Office Action dated Jul. 15, 2025.
PCT/US2022/026177 filed Apr. 25, 2022 International Search Report & Written Opinion dated Mar. 20, 2023.
U.S. Appl. No. 17/796,611, filed Jul. 29, 2022 Non-Final Office Action dated Mar. 20, 2025.
PCT/US2022/035565 filed Jun. 29, 2022 International Search Report and Written Opinion dated Sep. 27, 2022.
Peppas, "Hydrogels," Biomaterial Science: An Introduction to Materials in Medicine. 2nd Edition, pp. 100-107, Aug. 18, 2004.
Piyush Gupta et al. Hydrogels: from controlled release to pH-responsive drug delivery, May 2002, DDT vol. 7, No. 10, pp. 569-579. (Year: 2002).
RU 2015140616 filed Sep. 24, 2015 Office Action dated Feb. 21, 2018.
U.S. Appl. No. 12/091,916, filed Feb. 2, 2009 Final Office Action dated Sep. 22, 2011.
U.S. Appl. No. 12/091,916, filed Feb. 2, 2009 Non-Final Office Action dated May 10, 2011.
U.S. Appl. No. 12/091,916, filed Feb. 2, 2009 Non-Final Office Action dated Nov. 24, 2010.
U.S. Appl. No. 12/091,916, filed Feb. 2, 2009 Notice of Allowance dated Aug. 17, 2012.
U.S. Appl. No. 13/387,447, filed Mar. 22, 2012 Advisory Action dated Feb. 27, 2014.
U.S. Appl. No. 13/387,447, filed Mar. 22, 2012 Examiner's Answer dated Oct. 5, 2016.
U.S. Appl. No. 13/387,447, filed Mar. 22, 2012 Final Office Action dated Dec. 11, 2013.
U.S. Appl. No. 13/387,447, filed Mar. 22, 2012 Final Office Action dated Oct. 31, 2014.
U.S. Appl. No. 13/387,447, filed Mar. 22, 2012 Final Office Action dated Oct. 5, 2015.
U.S. Appl. No. 13/387,447, filed Mar. 22, 2012 Non-Final Office Action dated Jan. 15, 2013.
U.S. Appl. No. 13/387,447, filed Mar. 22, 2012 Non-Final Office Action dated Jul. 15, 2014.
U.S. Appl. No. 13/387,447, filed Mar. 22, 2012 Non-Final Office Action dated Jun. 6, 2013.
U.S. Appl. No. 13/387,447, filed Mar. 22, 2012 Non-Final Office Action dated Mar. 12, 2015.
U.S. Appl. No. 13/387,447, filed Mar. 22, 2012 Notice of Allowance dated Jul. 30, 2018.
U.S. Appl. No. 13/387,447, filed Mar. 22, 2012 Patent Board Decision dated Jun. 1, 2018.
U.S. Appl. No. 13/389,753, filed Mar. 20, 2012 Decision on Appeal dated Jun. 29, 2017.
U.S. Appl. No. 13/389,753, filed Mar. 20, 2012 Examiner's Answer dated Aug. 27, 2015.
U.S. Appl. No. 13/389,753, filed Mar. 20, 2012 Final Office Action dated Dec. 10, 2014.
U.S. Appl. No. 13/389,753, filed Mar. 20, 2012 Non-Final Office Action dated Jul. 21, 2014.
U.S. Appl. No. 13/389,753, filed Mar. 20, 2012 Notice of Allowance dated Jul. 5, 2017.
U.S. Appl. No. 13/516,660, filed Aug. 27, 2012 Advisory Action dated Nov. 19, 2019.
U.S. Appl. No. 13/516,660, filed Aug. 27, 2012 Advisory Action dated Sep. 22, 2016.
U.S. Appl. No. 13/516,660, filed Aug. 27, 2012 Board Decision dated Jan. 22, 2019.
U.S. Appl. No. 13/516,660, filed Aug. 27, 2012 Examiner's Answer dated Nov. 22, 2017.
U.S. Appl. No. 13/516,660, filed Aug. 27, 2012 Final Office Action dated Jun. 29, 2016.
U.S. Appl. No. 13/516,660, filed Aug. 27, 2012 Final Office Action dated Sep. 9, 2019.
U.S. Appl. No. 13/516,660, filed Aug. 27, 2012 Non-Final Office Action dated Jan. 8, 2020.
U.S. Appl. No. 13/516,660, filed Aug. 27, 2012 Non-Final Office Action dated Mar. 15, 2019.
U.S. Appl. No. 13/516,660, filed Aug. 27, 2012 Non-Final Office Action dated Mar. 8, 2016.

(56)                     References Cited

OTHER PUBLICATIONS

U.S. Appl. No. 13/516,660, filed Aug. 27, 2012 Notice of Allowance dated Oct. 27, 2020.
U.S. Appl. No. 13/582,698, filed Sep. 4, 2012 Non-Final Office Action dated Sep. 24, 2014.
U.S. Appl. No. 13/662,278, filed Oct. 26, 2012 Board Decision dated Aug. 23, 2018.
U.S. Appl. No. 13/662,278, filed Oct. 26, 2012 Examiner's Answer dated Jun. 2, 2017.
U.S. Appl. No. 13/662,278, filed Oct. 26, 2012 Final Office Action dated Feb. 20, 2015.
U.S. Appl. No. 13/662,278, filed Oct. 26, 2012 Final Office Action dated Oct. 19, 2016.
U.S. Appl. No. 13/662,278, filed Oct. 26, 2012 Non-Final Office Action dated Jul. 7, 2016.
U.S. Appl. No. 13/662,278, filed Oct. 26, 2012 Non-Final Office Action dated Sep. 12, 2014.
U.S. Appl. No. 13/662,278, filed Oct. 26, 2012 Non-Final Office Action dated Sep. 17, 2015.
U.S. Appl. No. 13/802,095, filed Mar. 13, 2013 Non-Final Office Action dated Aug. 15, 2014.
U.S. Appl. No. 13/802,095, filed Mar. 13, 2013 Notice of Allowance dated Nov. 28, 2014.
U.S. Appl. No. 14/681,023, filed Apr. 7, 2015 Non-Final Office Action dated Nov. 9, 2016.
U.S. Appl. No. 14/681,023, filed Apr. 7, 2015 Notice of Allowance dated Mar. 8, 2017.
U.S. Appl. No. 14/707,954, filed May 8, 2015 Non-Final Office Action dated Dec. 1, 2016.

U.S. Appl. No. 15/639,844, filed Jun. 30, 2017 Non-Final Office Action dated Jul. 10, 2019.
U.S. Appl. No. 15/639,844, filed Jun. 30, 2017 Notice of Allowance dated Aug. 13, 2019.
U.S. Appl. No. 15/669,697, filed Aug. 4, 2017 Non-Final Office Action dated Oct. 18, 2018.
U.S. Appl. No. 17/796,611, filed Jul. 29, 2022 Advisory Action dated Nov. 28, 2025.
U.S. Appl. No. 17/796,611, filed Jul. 29, 2022 Non-Final Office Action dated Jan. 8, 2026.
U.S. Appl. No. 18/019,464, filed Feb. 2, 2023 Notice of Allowance dated Nov. 25, 2025.
U.S. Appl. No. 18/019,647, filed Feb. 3, 2023 Non-Final Office Action dated Nov. 17, 2025.
U.S. Appl. No. 18/025,875, filed Mar. 10, 2023 Notice of Allowance dated Jan. 14, 2026.
U.S. Appl. No. 18/580,449, filed Jan. 19, 2024 Non-Final Office Action dated Feb. 2, 2026.
U.S. Appl. No. 18/604,394, filed Mar. 13, 2024 Final Office Action dated Jan. 23, 2026.
U.S. Appl. No. 18/641,181, filed Apr. 19, 2024 Non-Final Office Action dated Jan. 12, 2026.
U.S. Appl. No. 18/019,647, filed Feb. 3, 2023 Notice of Allowance dated Mar. 27, 2026.
U.S. Appl. No. 18/568,208, filed Dec. 7, 2023 Non-Final Office Action dated Apr. 1, 2026.
U.S. Appl. No. 18/604,394, filed Mar. 13, 2024 Notice of Allowance dated Apr. 20, 2026.
U.S. Appl. No. 18/641,181 filed Apr. 19, 2024 Final Office Action dated Apr. 28, 2026.

* cited by examiner

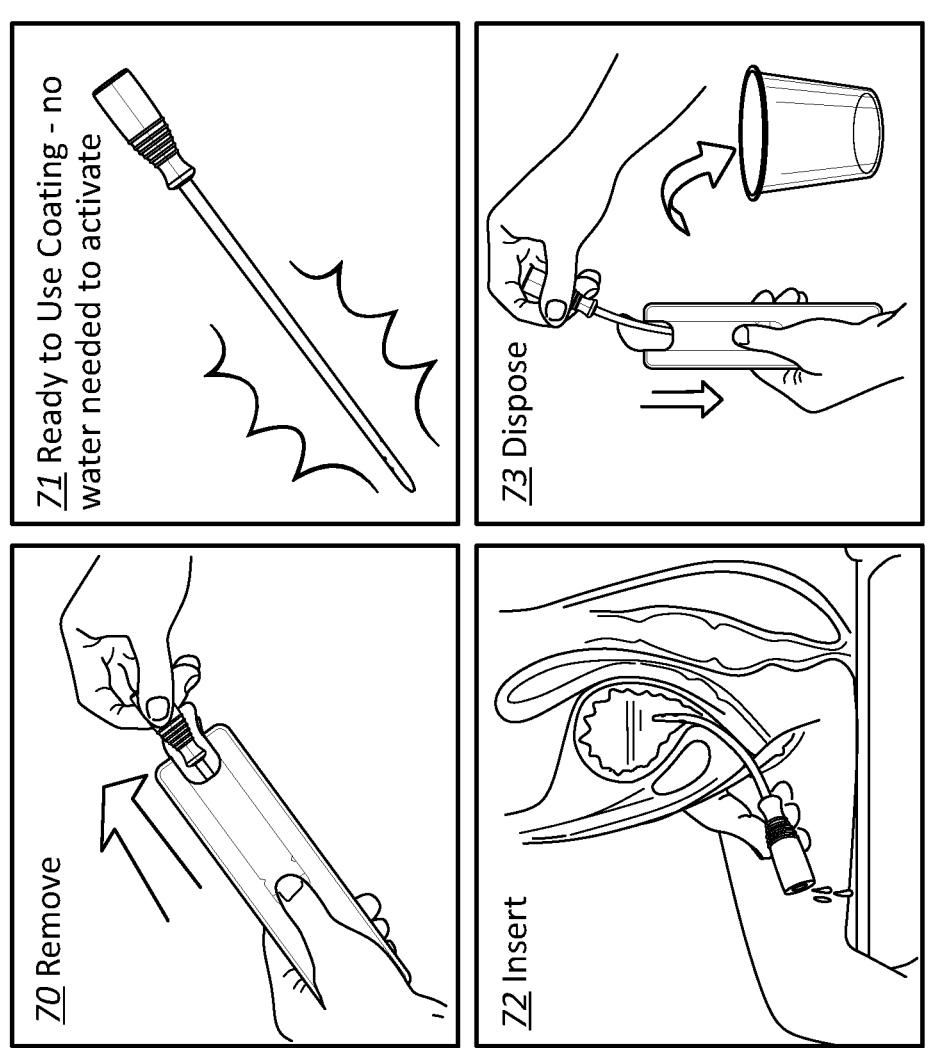
71 Ready to Use Coating - no water needed to activate
73 Dispose
70 Remove
72 Insert
*FIG. 2*
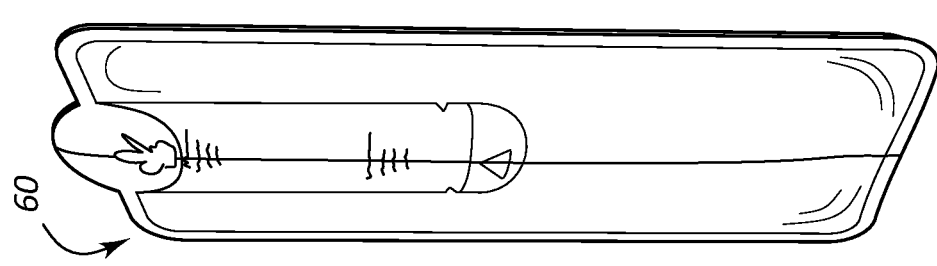
60
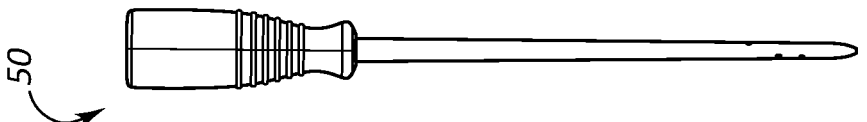
50

URINARY CATHETER

PRIORITY

This application is a continuation of U.S. patent application Ser. No. 17/114,275, filed Dec. 7, 2020, now U.S. Pat. No. 11,850,370, which is a continuation of U.S. patent application Ser. No. 15/506,723, a U.S. national stage application under 35 U.S.C. § 371 of International Application No. PCT/US2015/047026, filed Aug. 26, 2015, now U.S. Pat. No. 10,857,324, which claims the benefit of priority to U.S. Provisional Application No. 62/042,125, filed Aug. 26, 2014, each of which is incorporated by reference in its entirety into this application.

BACKGROUND

People suffering from neurogenic bladder disorders like spinal cord injury, spina bifida or multiple sclerosis, and non-neurogenic bladder disorders like obstruction due to prostate enlargement, urethral strictures or post-operative urinary retention, need to be continuously catheterized to empty their urinary bladders. However, continuous catheterization can lead to problems like urinary tract infections (UTI), urethral strictures or male infertility. Intermittent catheterization at regular intervals avoids many of the negative effects of continuous long term catheterization. There are four primary categories for intermittent catheters: (1) Bare Intermittents, (2) Hydrophilic Coated Intermittents, (3) Pre-Wetted Intermittents, and (4) Catheter in Bag or "Touchless" Intermittents.

Bare Intermittents require the use of an external lubrication method. These catheters are the least expensive and most commonly used. Typical materials include natural rubber (latex) (NRL), polyvinyl chloride (PVC) and silicone. The common lubrication method is a gel pack. The gel is either applied to the meatus of the urethra or the tip of the catheter itself. Hydrophilic Coated Intermittents have a lubricious coating applied typically to the first two-thirds of the shaft of the catheter and are activated by breaking a water sachet located inside the package prior to opening the package. When activated, the catheter is lubricious for insertion into the urethra. Potential issues with the Bare Intermittents and the Hydrophilic Coated Intermittents include the amount of mess they create (e.g., from the excess water from the water sachet and lubricant from the lubricant packs) and the time required for the user to complete the voiding process.

Pre-Wetted Intermittents may be packaged in a non-permeable package (e.g. foil, or rigid plastic) and suspended in water. Ideally, the catheters will stay wet over the length of their shelf life and may be much like hydrophilic coated intermittents that have been activated by water. Pre-Wetted Intermittents may have a lubricious coating in addition to being packaged in water. This can eliminate the process step of lubricating the catheter, but may still some mess to contend with (e.g., from the water stored in the package), and the coating may dry out over its shelf life making it unusable.

Catheter in Bag or "Touchless" Intermittents may include either a Bare Intermittent or Hydrophilic Coated Intermittent. There may be an insertion tip on an end of the bag with the distal end of the catheter captured in the insertion tip. Upon use, the user may advance the catheter out of the bag using the insertion tip to help guide the catheter into the urethra. The bag may be used for urine collection. However, use of a Touchless Catheter may be cumbersome and difficult.

The following are references relating to coatings: U.S. Pat. Nos. 6,673,053, 8,011,505, and 6,059,107, which are incorporated by reference herein in their entireties.

SUMMARY

The urinary catheters described herein provide a novel type of intermittent catheter not currently available. The coating may exhibit hygroscopic characteristics, described herein as the characteristic or intention of the coating to not only retain the moisture inherent in the coating but also to attract moisture from the environment. The coating may exhibit hydrophilic characteristics. The coating described herein is an improved formulation that is applied in a wet state and stays wet for an extended period of time. Accordingly, the urinary catheters described herein do not require an additional lubricant or wetting component, such as a water sachet or gel package, to accompany the catheters in the containers. The urinary catheters described herein may be packaged individually in a discrete container, such as an opaque foil. These and other features of embodiments of the present invention will become more fully apparent from the following description and appended claims, or may be learned by the practice of embodiments of the invention as set forth hereinafter.

In one embodiment a urinary catheter may include a catheter shaft attached to a handle. The urinary catheter may also include a hygroscopic and/or hydrophilic coating disposed on an outer surface of the catheter shaft. The coating may include a hydrogel, glycerin or water, and a polyethylene glycol (PEG). In one embodiment, the hydrogel may be LUBRAJEL® RR CG hydrogel or LUBRAJEL® RR hydrogel, and the PEG may be one or both of PEG 300 and PEG 400. In embodiments described herein with respect to specific hydrogels (e.g., LUBRAJEL® RR CG hydrogel), other hydrogels (e.g., LUBRAJEL® RR hydrogel) are contemplated as being substituted for, or added to, the specified hydrogel. Likewise, in embodiments described herein with respect to specific polyethylene glycols (e.g., PEG 300), other polyethylene glycols are contemplated as being substituted for, or added to, the specified polyethylene glycol.

In one embodiment, a urinary catheter includes a catheter shaft attached to a handle, and a first coating disposed on an outer surface of the catheter shaft, the first coating including a hydrogel or polyacrylic acid (PAA), glycerin and/or water, and polyethylene glycol (PEG), the first coating exhibiting hygroscopic and/or hydrophilic characteristics. In one embodiment, the outer surface of the catheter shaft includes a second coating over which the first coating is disposed. In one embodiment, the second coating is a hydrophilic coating.

In one embodiment, the coating formulations described herein provide non-adhesion (or anti-blocking) toward the packaging material. In one embodiment, a catheter with the coating can be sterilized through electron beam ("e-beam") sterilization or ethylene oxide (EtO) sterilization. In one embodiment, an additional ultraviolet (UV)-curable silicone film can be applied over a catheter with the coating described herein. The silicone film may restrict the coating on the catheter. In one embodiment, the film may be moved, e.g., toward the catheter handle, thereby acting as a touchless layer while maintaining the lubricity of the catheter. In one embodiment, the UV-curable silicone film is disposed on the coating via an UV curing process.

In one embodiment of the packaged urinary catheter, a coating formulation (e.g., a formulation for a base coating and/or outer coating) for the catheter may include LUBRAJEL® RR CG hydrogel in a range of 15 wt % to 35 wt %, water in a range of 10 wt % to 45 wt %, and PEG in a range of 20 wt % to 75 wt %. In one embodiment, a coating formulation may include LUBRAJEL® RR CG hydrogel in a range of 20 wt % to 30 wt %, water in a range of 20 wt % to 30 wt %, and PEG 400 in a range of 40 wt % to 60 wt %. In one embodiment, the coating formulation may include LUBRAJEL® RR CG hydrogel in a range of 22 wt % to 26 wt %, water 25 wt %, and PEG 400 in a range of 49 wt % to 53 wt %. In one embodiment the coating formulation may include LUBRAJEL® RR CG hydrogel at 23.5 wt %, water at 25 wt %, and PEG 400 at 51.5 wt %. In one embodiment, a coating formulation may include LUBRAJEL® RR CG hydrogel in a range of 20 wt % to 30 wt %, glycerin in a range of 20 wt % to 30 wt %, and PEG 400 in a range of 40 wt % to 60 wt %. In one embodiment, the coating formulation may include LUBRAJEL® RR CG hydrogel in a range of 20 wt % to 30 wt %, glycerin in a range of 40 wt % to 60 wt %, and PEG 300 in a range of 20 wt % to 30 wt %. In one embodiment, the coating formulation may include LUBRAJEL® RR CG hydrogel in a range of 10 wt % to 35 wt %, glycerin in a range of 25 wt % to 75 wt %, PEG 300 in a range of 25 wt % to 65 wt %, and PEG 400 in a range of 25 wt % to 50 wt %. In one embodiment, a coating formulation may include LUBRAJEL® RR CG hydrogel in a range of 20 wt % to 30 wt %, glycerin in a range of 40 wt % to 60 wt %, propylene glycol (PEG) in a range of 10 wt % to 15 wt %, and ethanol (anhydrous) in a range of 10 wt % to 15 wt %. In one embodiment, the LUBRAJEL® RR CG hydrogel is 50 wt %, the glycerin is 25 wt %, and both the PEG and ethanol are 12.5 wt %.

In one embodiment, a coating formulation may include LUBRAJEL® RR hydrogel in a range of 15 wt % to 35 wt %, glycerin in a range of 15 wt % to 30 wt %, and PEG 400 in a range of 35 wt % to 70 wt %. In one embodiment, the coating formulation may include LUBRAJEL® RR hydrogel at 25 wt %, glycerin at 25 wt %, and both PEG 300 and PEG 400 at 25 wt %. In one embodiment, the coating formulation may include LUBRAJEL® RR hydrogel at 40 wt %, glycerin at 15 wt %, PEG 300 at 15 wt %, and PEG 400 at 30 wt %. In one embodiment, a coating formulation may include LUBRAJEL® RR in a range of 20 wt % to 30 wt %, water in a range of 20 wt % to 30 wt %, and PEG 400 in a range of 40 wt % to 60 wt %.

In one embodiment, a coating formulation may include polyacrylic acid (PAA) in a range of 0.2 wt % to 3 wt %, glycerin in a range of 15 wt % to 25 wt %, water in a range of 20 wt % to 30 wt %, and PEG 400 in a range of 40 wt % to 60 wt %. In one embodiment, a coating formulation may include PAA in a range of 0.1 wt % to 2.5 wt %, water in a range of 10 wt % to 45 wt % and PEG, such as PEG 300 and/or PEG 400, in a range of 20 wt % to 65 wt %.

In one embodiment, a silicone film may be formed over a coating on a catheter. In one embodiment, a method of forming a catheter with a coating includes dipping a coated catheter, such as a hydrophilic coated catheter, into a solution containing any of the coating formulations herein, such as a coating formulation including PAA, water, and PEG or a coating formulation including hydrogel, glycerin and/or water, and PEG, then dipping the twice-coated catheter into a UV curable solution, then exposing the coated areas to a UV source, and then directly placing the catheter into a package. In one embodiment, the hydrophilic coated catheter is dipped into a PAA/water/PEG solution for a dwell time in a range of 0.1 seconds to 10 seconds. In one embodiment, after the catheter is dipped into the PAA/water/PEG solution, it is dipped into a silicone solution with UV curable agents several times to achieve a desired film thickness. In one embodiment, the desired thickness is 0.001 in. to 0.004 in. In one embodiment, the catheter is dipped into the silicone solution with UV curable agents 2 to 6 times. In one embodiment, after being dipped into the silicone solution with UV curable agents, the catheter is exposed to a UV source, such as a UV light, in a time range of 0.3 min to 2.0 min. In one embodiment, following the exposure to the UV source, the catheter is placed directly into a film, foil, and/or Tyvek package without a further drying process.

In one embodiment, a method of making a urinary catheter includes applying a first coating to a catheter shaft, the first coating comprising a hydrogel or polyacrylic acid (PAA), glycerin and/or water, and polyethylene glycol (PEG) to form a coated catheter, and placing the coated catheter into a package comprising a gas impermeable foil material. In one embodiment, the catheter shaft includes a base hydrophilic coating, and the first coating is applied over the base hydrophilic coating. In one embodiment, the applying includes dipping the catheter shaft with the base hydrophilic coating into a solution containing a formulation of the first coating. In one embodiment, the first coating formulation comprises only the PAA, the water, and the PEG, further comprising dipping the coated catheter into a silicone solution including ultraviolet (UV) curable agents to form a silicone film over the first coating. In one embodiment, the method includes exposing the silicone film to a UV light source for a period of time to cure the silicone solution.

In one embodiment, the urinary catheter may include an eyelet or a plurality of staggered, opposing eyelets (e.g., 3, 4, 5, 6, 7, 8, or more eyelets) proximal to a catheter tip, the eyelets may be arranged in a variety of ways, including circumferentially positioned 90 degrees apart and positioned in a non-overlapping configuration. In one embodiment, the urinary catheter shaft includes a funnel shaped proximal end and ridges configured to facilitate gripping. In one embodiment, the urinary catheter may have a coating that exhibits hygroscopic characteristics. In another embodiment, the urinary catheter may have a coating that exhibits hydrophilic characteristics.

In one embodiment, a packaged urinary catheter may include a container and a urinary catheter. The urinary catheter may include a catheter shaft attached to a handle and a coating disposed on an outer surface of the catheter shaft. In one embodiment, the coating may include a hydrogel, glycerin or water, and PEG, such as one or both of PEG 300 and PEG 400. In one embodiment, the coating may include PAA, glycerin, water, and PEG, such as PEG 300 and/or PEG 400. In one embodiment, the coating may include PAA, water, and PEG, such as PEG 300 and/or PEG 400.

In one embodiment of the packaged urinary catheter, the container may include a gas impermeable foil material. In one embodiment of the packaged urinary catheter, the container may include an adhesive tab covering a perforated section of the foil material, the adhesive tab may include a pull loop. In one embodiment, the container may include a water sachet, gel package, or other type of lubricant therein. In one embodiment, the container may include a moisture source (in contact or separated from the catheter) from which a hygroscopic coating and/or a hydrophilic coating on the urinary catheter may absorb or obtain moisture. In one embodiment of the packaged urinary catheter, the container does not include any water sachet, gel package, or other type of lubricant or moisture source therein.

In one embodiment, a method of catheterizing may include obtaining a urinary catheter that may include a handle and a catheter shaft. The catheter shaft may include a hydrophilic coating and/or a hygroscopic coating on an outer surface thereof. In one embodiment, the coating may include a coating formulation described herein. The method may further include inserting the urinary catheter into a bladder. In one embodiment, the method of catheterizing may include obtaining the urinary catheter from a container in which the urinary catheter has been stored. In one embodiment, the method of catheterizing does not include application of a lubricant or water to the catheter shaft at any time prior to insertion into the bladder, including while in the package.

BRIEF DESCRIPTION OF THE DRAWINGS

The disclosed systems and methods can be better understood with reference to the following drawings. The components in the drawings are not necessarily to scale. It is appreciated that these drawings depict only typical embodiments of the invention and are therefore not to be considered limiting of its scope. Example embodiments of the invention will be described and explained with additional specificity and detail through the use of the accompanying drawings in which:

FIG. 2 shows one embodiment of a urinary catheter according to embodiments described herein, and illustrates the exemplary use of a female urinary catheter according to embodiments described herein.

Figure 1:
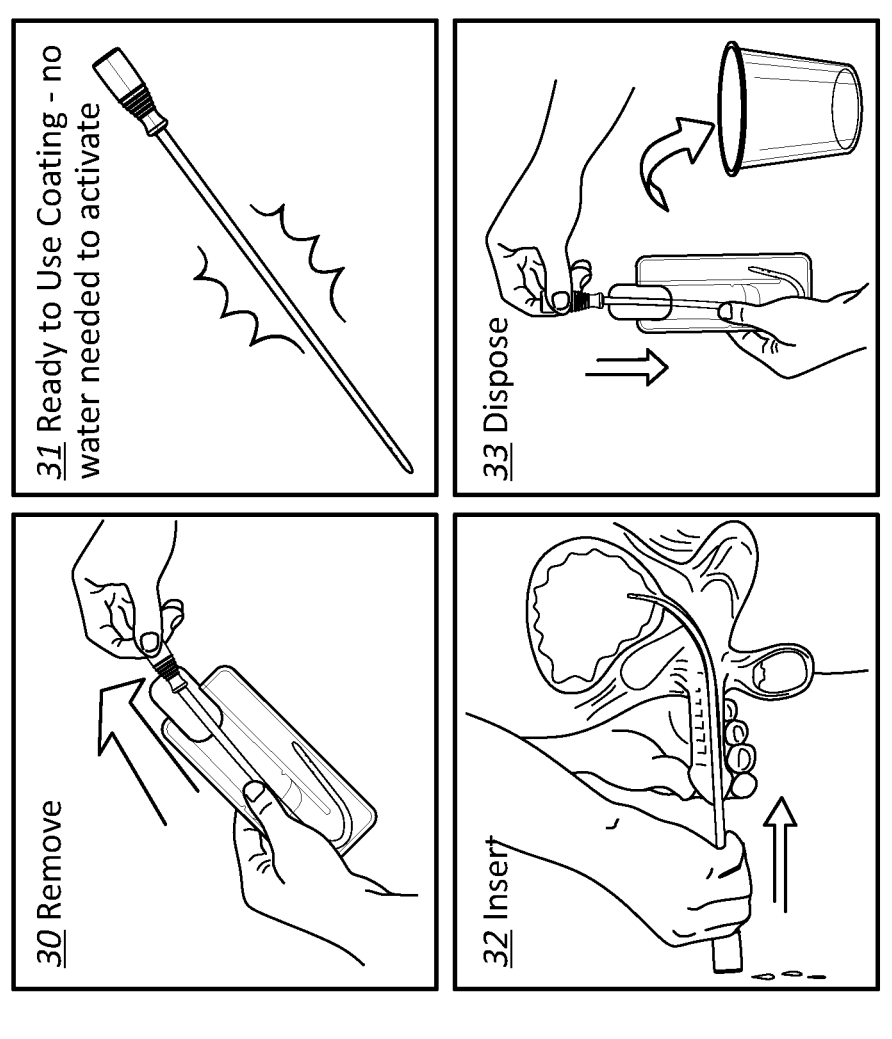
FIG. 1 shows one embodiment of a urinary catheter according to embodiments described herein, and illustrates the exemplary use of a male urinary catheter according to embodiments described herein.
Figure 1:
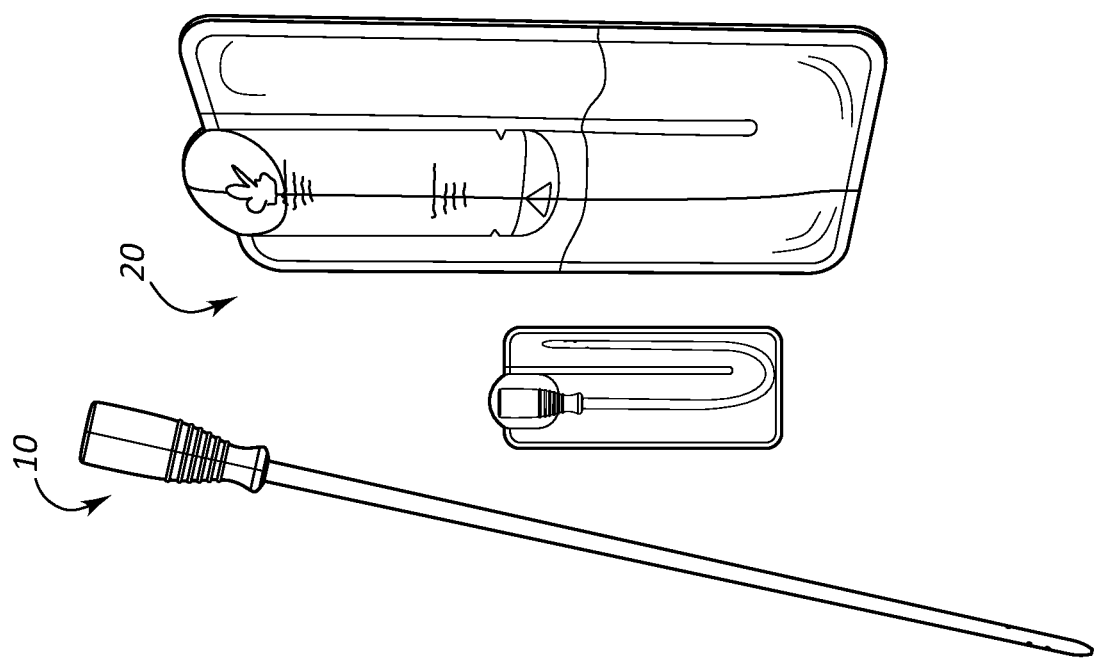

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but rather the intention is to cover all modifications, equivalents, and alternatives falling within the spirit and scope of the invention as defined by the appended claims.

DETAILED DESCRIPTION

The following description and accompanying figures, which describe and show certain embodiments, are made to demonstrate, in a non-limiting manner, several possible configurations of a catheter according to various aspects and features of the present disclosure. While the description herein, by way of example, is focused primarily on a description of a urinary catheter and associated methods, the inventions described herein are not so limited and the concepts may be applied to other types of catheters and devices.

The urinary catheter described herein is ready to use immediately when the container is opened, and may be inserted by the patient or patient's caregiver in a homecare setting, managed care/assisted living setting, or in hospitals. Within the homecare setting, the catheter can be used in a range of restroom and non-restroom environments. FIGS. 1 and 2 show urinary catheters and methods of using them according to embodiments described herein.

FIG. 1 illustrates the male urinary catheter 10, the packaging 20 for the male urinary catheter 10, and the exemplary use (e.g., steps 30-33) thereof according to embodiments described herein, and FIG. 2 illustrates the female urinary catheter 50, the packaging 60 for the female urinary catheter 50, and the exemplary use (e.g., steps 70-73) thereof according to embodiments described herein. The methods shown in FIGS. 1 and 2 do not require the user to take any step to apply lubricant, such as water or gel, directly to the catheter, either while the catheter is within the package or when after the package has been opened. Accordingly, the user may move directly from the step of removing the catheter from the package 30, 70 to the step of inserting the catheter 32, 72 without an intervening direct lubrication or hydration step (see example steps 31, 71, which indicate the catheter is ready to use upon removing from the packaging, without requiring the addition of water or lubricant). The catheters used in FIGS. 1 and 2 can be catheters of any of the embodiments discussed herein, e.g., the catheters may have a coating formulation that exhibits hygroscopic and/or hydrophilic characteristics (which eliminates the need for the user to take steps to lubricate or hydrate the catheter). In the case of a catheter with a hygroscopic coating, while some water from the surrounding environment may be naturally attracted by the coating, this is not considered a direct lubrication or hydration step taken in the method. After use, the catheter 10, 50 may be disposed of according to sanitary procedure. Example disposal steps 33, 73 depict one possible procedure for disposal, including returning the catheter to the packaging and discarding the packaging in a trash can or similar receptacle. The packaging may be sealable (e.g., by adhesive, zip-lock, etc.), such that the package may be sealed shut after the urinary catheter is disposed therein.

Figures 3A, 3B:
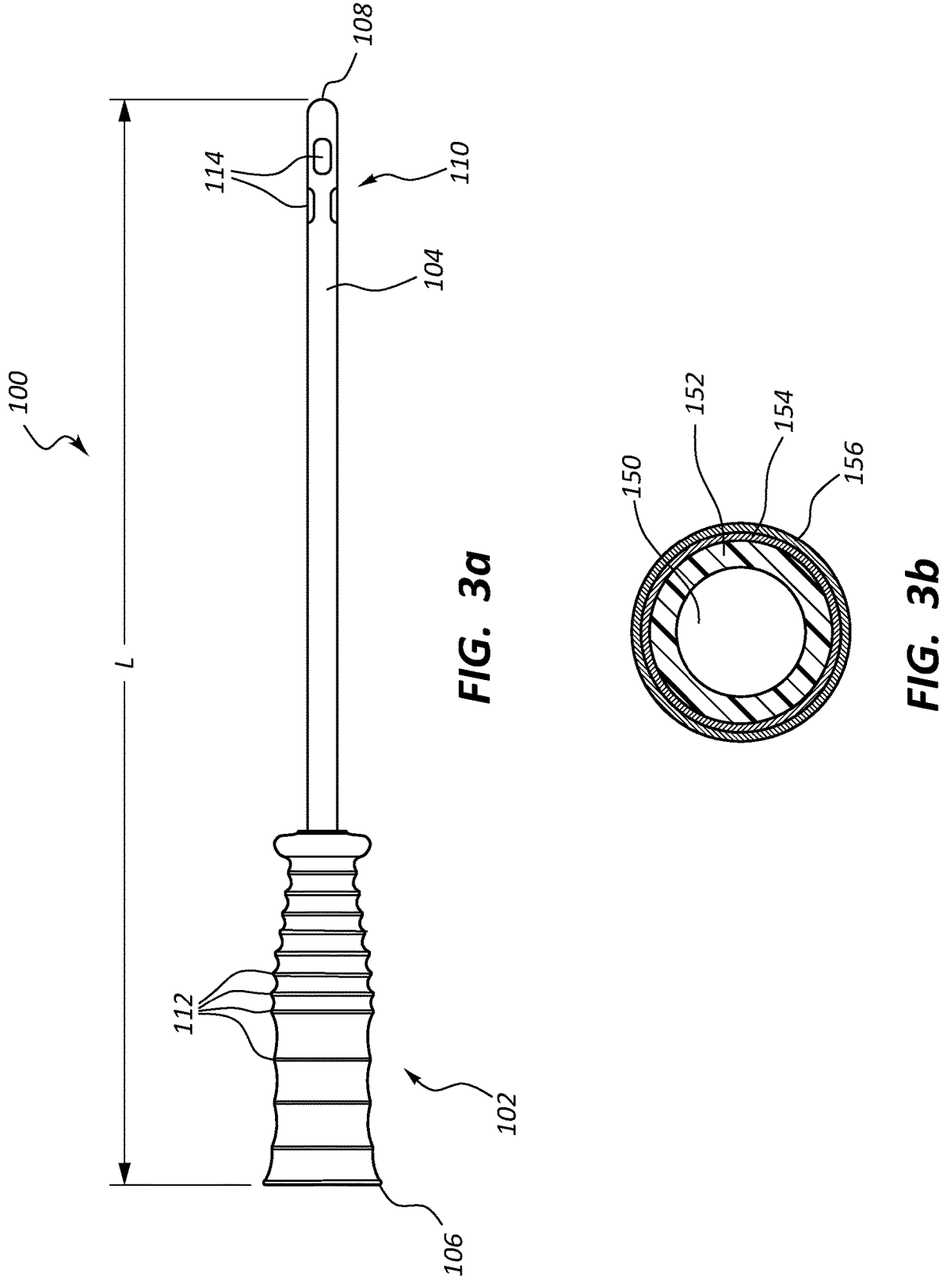
FIG. 3*a* is a urinary catheter according to embodiments described herein.
FIG. 3*b* is a cross sectional view of the urinary catheter shaft according to embodiments described herein.

Referring to FIG. 3*a*, in one embodiment, a urinary catheter 100 includes a handle 102 on a proximal end and a catheter shaft 104 attached to the handle 102. The urinary catheter may be one of a variety of different types of urinary catheters. The handle 102 may have a funnel-like shape 106 on the proximal end thereof, and may be adapted to connect to drain bags, extension tubes, and/or the like. Also, handle shapes other than a funnel-like shape may be utilized within the scope of the present disclosure. The handle 102 may indicate the size of the catheter, and may have a color to indicate sex (e.g., pink for female, blue for male). In one embodiment, the catheter shaft 104 is made from a silicone material. In one embodiment, the silicone material has a durometer in the range of shore 70 A to 85 A and a thickness in the range of 1.1 mm to 2.27 mm. It is appreciated that the composition of the catheter shaft 104 may include other materials that possess similar physical properties which falls within scope of the present disclosure. In one embodiment, the column strength of the catheter shaft 104 is configured or designed to facilitate insertion, e.g., requiring less force than current polyvinyl chloride (PVC) catheters. In one embodiment, the catheter 100 will be at least partially transparent to an unaided eye.

Referring to FIGS. 3*a* and 3*b*, the catheter 100 includes openings 114 in a distal end 110 that are in fluid communication with a lumen 150 that extends through the catheter shaft and handle. In one embodiment, the catheter includes four staggered, opposing eyelets 114 proximal to a catheter tip 108, the eyelets 114 are circumferentially positioned 90 degrees apart and positioned in a non-overlapping configuration. It is appreciated that other numbers and configurations of openings fall within the scope of the present disclosure. The handle 102 includes ridges 112 to provide a gripping surface for easier gripping and handling. The catheter shaft 104 may include the lumen 150, a catheter wall 152, a hydrophilic base coating 154 (e.g., polyacrylic acid), and may also include a pre-hydrated outer coating applied thereover 156 (e.g., over the base coating). The pre-hydrated coating may remain wet without the application of water or lubricant gel.

In one embodiment, the catheter 100 includes a hygroscopic coating 156 (e.g. a top or outer pre-hydrated coating). In one embodiment, the catheter 100 includes a hygroscopic coating 156 including a hydrogel, glycerin, water, and a polyethylene gylcol (PEG) with a molecular weight equal to or less than 600, for example one or more of polyethylene glycol (PEG) 300 and PEG 400. In one embodiment, the hydrogel is a LUBRAJEL® hydrogel. For coating embodiments described herein, the type of LUBRAJEL® hydrogel may be LUBRAJEL® RR CG hydrogel, having an INCI name of Glycerin (and) Glyceryl Acrylate/Acrylic Acid Copolymer (and) Propylene Glycol. For coating embodiments described herein, the type of LUBRAJEL® hydrogel may be LUBRAJEL® RR hydrogel. In one embodiment, the catheter includes a coating including a hydrogel (e.g., LUBRAJEL® hydrogel), glycerin, propylene glycol (PEG), and ethanol. In one embodiment, the catheter includes a coating including a hydrogel (e.g., LUBRAJEL® hydrogel), glycerin or water, and propylene glycol (PEG), such as PEG 300 and/or PEG 400. In one embodiment, the catheter may be sold and packaged in sizes ranging in diameter from 8 Fr to 24 Fr (e.g., 8 Fr, 10 Fr, 12 Fr, 14 Fr, 16 Fr, 18 Fr, 20 Fr, 22 Fr, 24 Fr) with a length L of greater than 155 mm and intended for female use. However, other sizes of catheters may also be used. In other embodiments, the catheter may be sold and packaged in various sizes for male use.

In one embodiment, the base coating 154 and/or the outer coating 156 may be applied to the catheter shaft by a method involving either dipping, brushing, spraying or extruding. It is appreciated that other methods of applying one or both of the coatings to the catheter may be utilized and fall within the scope of the present disclosure. In one embodiment, the catheter shaft may be dipped into a volume of coating formulation. In one embodiment, the components of the coating formulation are mixed together, then the catheter shaft dipped into the volume thereof. For example, the hydrophilic coating or outer coating may be produced by mixing LUBRAJEL® with water and PEG for between 1.5 to 4.0 hours. The catheter (with or without a base coating) may be dipped into the coating solution and left to dwell for between 0.1-10 seconds. The catheter may then be removed from the coating solution and directly placed into packaging without any further drying process.

In one embodiment, the eyelets are punched into the catheter prior to dipping into one or more coating formulations to form a coating (e.g., a base coating and/or outer coating) such that both interior and exterior of the catheter is coated, i.e., at least a portion of the outer surface of the catheter shaft and at least a portion of the inner wall defining the lumen 150 of the catheter shaft are coated with the coating formulation. In other embodiments, one or more coating formulations may be brushed onto an outer surface of the catheter shaft (e.g., doctor blade method). In one embodiment, the coating (e.g., the base coating and/or the outer coating) is only on the catheter shaft (either the entire catheter shaft or a distal portion thereof), not on the handle. The coating described herein provides the urinary catheter with a coefficient of friction (COF) in the range of 0.03 to 0.15.

In one embodiment, a coating formulation (e.g., a formulation for a base coating and/or outer coating) for the catheter may include LUBRAJEL® RR CG hydrogel in a range of 15 wt % to 35 wt %, water in a range of 10 wt % to 45 wt %, and PEG in a range of 20 wt % to 75 wt %. In one embodiment, a coating formulation may include LUBRAJEL® RR CG hydrogel in a range of 15 wt % to 35 wt %, water in a range of 2 wt % to 45 wt %, and PEG in a range of 20 wt % to 75 wt %. In one embodiment, a coating formulation may include LUBRAJEL® RR CG hydrogel in a range of 20 wt % to 30 wt %, water in a range of 20 wt % to 30 wt %, and PEG 400 in a range of 40 wt % to 60 wt %. In one embodiment, the coating formulation may include LUBRAJEL® RR CG hydrogel in a range of 22 wt % to 26 wt %, water 25 wt %, and PEG 400 in a range of 49 wt % to 53 wt %. In one embodiment the coating formulation may include LUBRAJEL® RR CG hydrogel at 23.5 wt %, water at 25 wt %, and PEG 400 at 51.5 wt %. In one embodiment, a coating formulation may include LUBRAJEL® RR CG hydrogel in a range of 20 wt % to 30 wt %, glycerin in a range of 20 wt % to 30 wt %, and PEG 400 in a range of 40 wt % to 60 wt %. In one embodiment, the coating formulation may include LUBRAJEL® RR CG hydrogel in a range of 20 wt % to 30 wt %, glycerin in a range of 40 wt % to 60 wt %, and PEG 300 in a range of 20 wt % to 30 wt %. In one embodiment, the coating formulation may include LUBRAJEL® RR CG hydrogel in a range of 10 wt % to 35 wt %, glycerin in a range of 25 wt % to 75 wt %, PEG 300 in a range of 25 wt % to 65 wt %, and PEG 400 in a range of 25 wt % to 50 wt %. In one embodiment, a coating formulation may include LUBRAJEL® RR CG hydrogel in a range of 20 wt % to 30 wt %, glycerin in a range of 40 wt % to 60 wt %, propylene glycol (PEG) in a range of 10 wt % to 15 wt %, and ethanol (anhydrous) in a range of 10 wt % to 15 wt %. In one embodiment, the LUBRAJEL® RR CG hydrogel is 50 wt %, the glycerin is 25 wt %, and both the PEG and ethanol are 12.5 wt %.

In one embodiment, a coating formulation may include LUBRAJEL® RR hydrogel in a range of 15 wt % to 35 wt %, glycerin in a range of 15 wt % to 30 wt %, and PEG 400 in a range of 35 wt % to 70 wt %. In one embodiment, the coating formulation may include LUBRAJEL® RR hydrogel at 25 wt %, glycerin at 25 wt %, and both PEG 300 and PEG 400 at 25 wt %. In one embodiment, the coating formulation may include LUBRAJEL® RR hydrogel at 40 wt %, glycerin at 15 wt %, PEG 300 at 15 wt %, and PEG 400 at 30 wt %. In one embodiment, a coating formulation may include LUBRAJEL® RR in a range of 20 wt % to 30 wt %, water in a range of 20 wt % to 30 wt %, and PEG 400 in a range of 40 wt % to 60 wt %.

In one embodiment, a coating formulation may include polyacrylic acid (PAA) in a range of 0.2 wt % to 3 wt %, glycerin in a range of 15 wt % to 25 wt %, water in a range of 20 wt % to 30 wt %, and PEG 400 in a range of 40 wt % to 60 wt %. In one embodiment, a coating formulation may include PAA in a range of 0.1 wt % to 2.5 wt %, water in a range of 10 wt % to 45 wt % and PEG, such as PEG 300 and/or PEG 400, in a range of 20 wt % to 65 wt %.

In one embodiment, a silicone film may be formed over a coating on a catheter. In one embodiment, a method of forming a catheter with a coating includes dipping a coated catheter, such as a hydrophilic coated catheter, into a solution containing any of the coating formulations herein, such as a coating formulation including PAA, water, and PEG or a coating formulation including hydrogel, glycerin and/or water, and PEG, then dipping the twice-coated catheter into a UV curable solution, then exposing the coated areas to a UV source, and then directly placing the catheter into a package. In one embodiment, the hydrophilic coated catheter is dipped into a PAA/water/PEG solution for a dwell time in a range of 0.1 seconds to 10 seconds. In one embodiment, after the catheter is dipped into the PAA/water/PEG solution, it is dipped into a silicone solution with UV curable agents several times to achieve a desired film thickness. In one embodiment, the desired thickness is 0.001 in. to 0.004 in. In one embodiment, the catheter is dipped into the silicone solution with UV curable agents 2 to 6 times. In one embodiment, after being dipped into the silicone solution with UV curable agents, the catheter is exposed to a UV source, such as a UV light, in a time range of 0.3 min to 2.0 min. In one embodiment, following the exposure to the UV source, the catheter is placed directly into a film, foil, and/or Tyvek package without a further drying process. The silicone with UV curable agents, after curing forms a film that covers the coating on the catheter and can be moved when the catheter is ready for insertion. This acts to facilitate insertion without touching the lubricious coating while maintaining the lubricity of the coating on the catheter.

Referring to FIGS. 4a-7, the urinary catheters described herein may be packaged individually in discrete containers to form packaged urinary catheters such as the packaged urinary catheter 200. For example, the packaging or container may be opaque and resemble an item distinct from a urinary catheter, such as a food item or the like. In one embodiment, the packaging or container 210 is formed of and/or includes a foil material. In other embodiments, the container 210 includes a polyolefin film (e.g., polyethylene (PE)), an ethylene vinyl acetate (EVA) film, and/or a metallized polypropylene (PP) film. In one embodiment, the packaging material is gas impermeable. In one embodiment, of the lubricity of the coating is maintained or improved over time in the packaging while at normal environmental storage conditions. The packaging 210 may have a color to indicate sex (e.g., pink for female, blue for male). In one embodiment, the packaging 210 can be sterilized either by Electron Beam Processing (E-beam) or treatment with Ethylene Oxide (EtO).

Figures 4A, 4B, 4C:
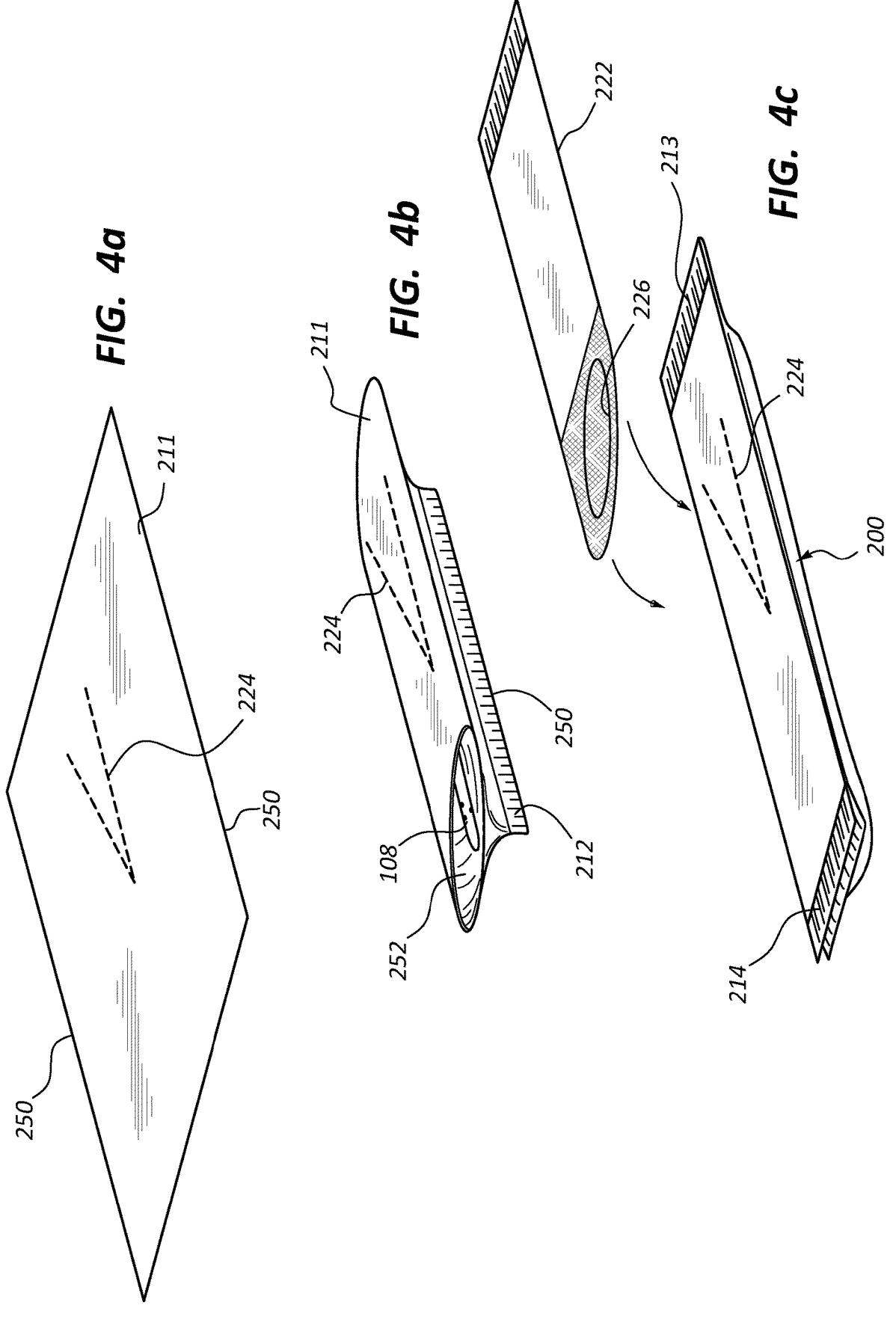
FIG. 4*a* is a first step in a method of making the container for a urinary catheter according to embodiments described herein.
FIG. 4*b* is a second step in a method of making the container for a urinary catheter according to embodiments described herein.
FIG. 4*c* is a third step in a method of making the container for a urinary catheter according to embodiments described herein.
Figure 5:
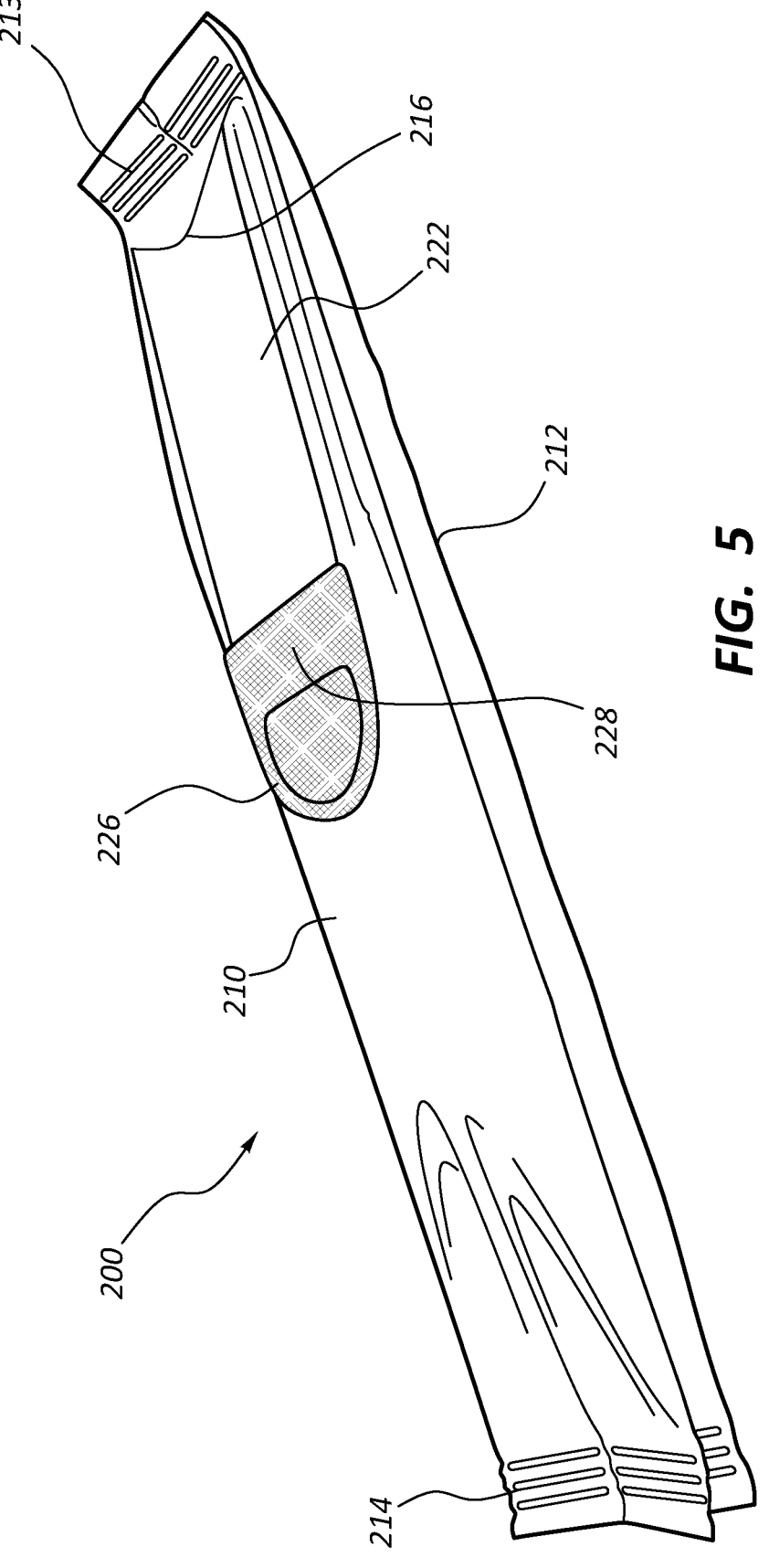
FIG. 5 is a container for a urinary catheter of FIGS. 4-7, according to embodiments described herein in a closed state.
Figure 6:
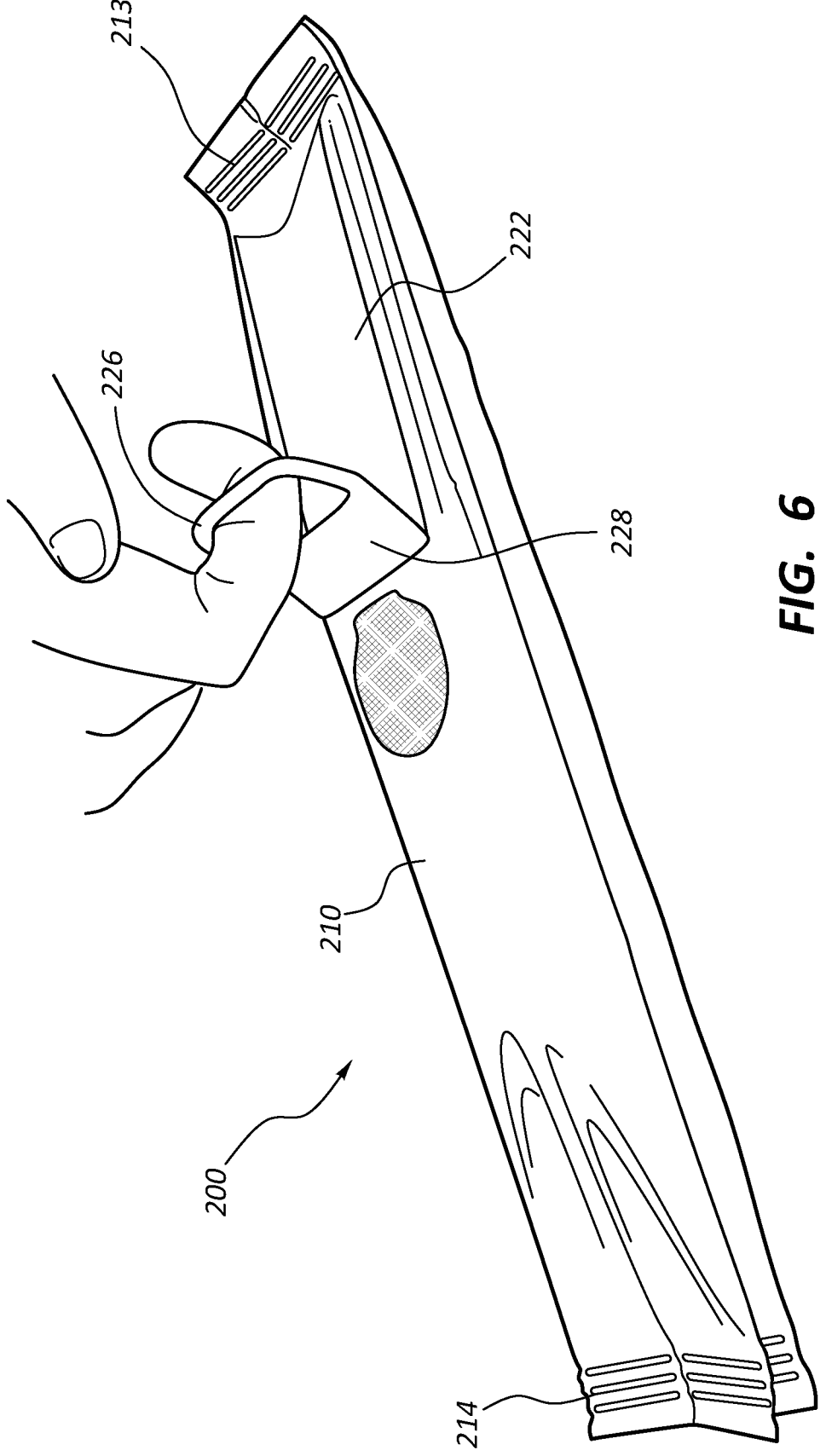
FIG. 6 is the container for a urinary catheter of FIGS. 4-7, being opened according to embodiments described herein.
Figure 7:
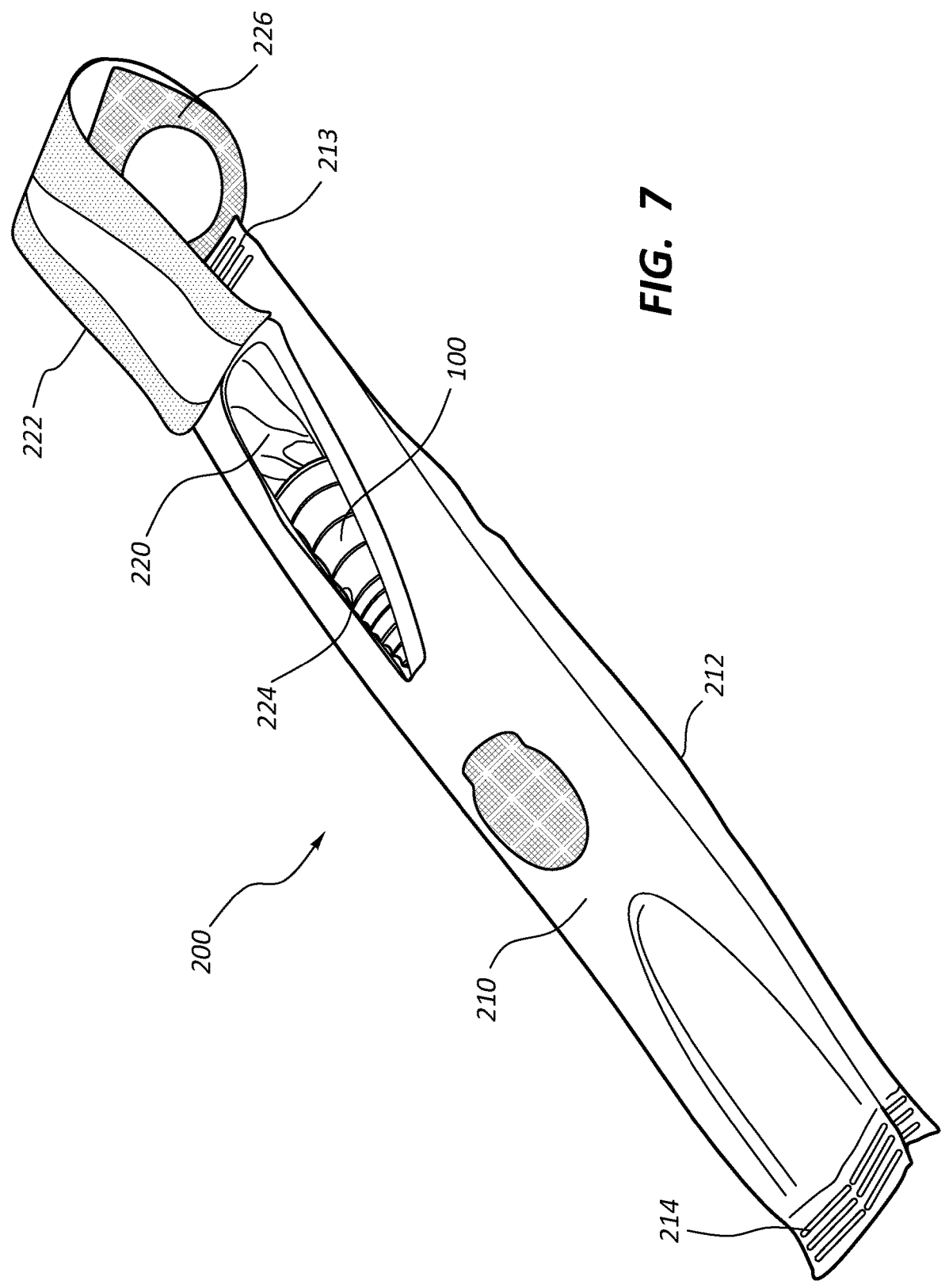
FIG. 7 is the container of FIGS. 4-7 in an opened state, revealing the urinary catheter handle.

Referring to FIGS. 4a-4c, a method of manufacturing the packaging for a catheter, discussed herein, including the following steps of producing the package, performed in any order: providing a sheet material 211; providing a weakened area 224, such as a perforation or kiss cut, in the sheet material by cutting the material; folding over and connecting the longitudinal edges 250 of the sheet 211 to form a back seam 212 and a cavity 252 (FIG. 4b). Disposing a catheter 100 within the cavity 252 and enclosed therein by sealing the ends to create a first end seam 213, and a second end seam 214 (FIG. 4c). Adhering an adhesive tab 222 over the weakened area 224.

In one embodiment, this arrangement may be similar to a packaging such as might be used on a candy bar, with overlapping edges forming a seam along the back and seams at the edges. The overlapping edges may be folded to one side or the other. The packaging material may present a smooth front. The front of the container may include a sealed opening 220, covered by an adhesive tab 222 (FIG. 4c). The sealed opening may include a weakened area 224, such as a perforation or kiss cut, in the packaging material covered by an adhesive portion of the adhesive tab 222. The adhesive tab 222 may include features, such as a pull loop 226, to hang the container after exposing the catheter 100 in the packaging in order to facilitate user access to the catheter 100 in the container 210. The adhesive tab 222 may be formed of a material such as polyethylene terephthalate (PET) substrate, with an adhesive, such as an S6 adhesive, on part of or the entire bottom surface of the adhesive tab. In one embodiment, the adhesive tab may include a label. The label may have artwork printed on or otherwise associated with a top surface of the label. The label may be stamped out of a rollstock of material and a varnish may be applied over approximately 1 inch of the distal end 228 of the label to facilitate lifting to begin the peeling process.

The adhesive tab may include a pull loop 226 to facilitate opening of the container 210, which after opening (FIG. 7) may be positioned over a hook or the like in order to suspend the container for ease of use. Alternatively, the adhesive portion of the adhesive tab 222 may be pressed against a hard surface (e.g., a wall, table, desk, equipment, etc.) in order to prevent movement of the container. In one embodiment, the catheter 100 may be reinserted into the container 210 and the adhesive tab 222 pressed back over the opening 220 to re-seal the container 210 for disposal in another location. The embodiment of FIGS. 4-7 is easy to open by simply putting a finger through the pull loop 226 (FIG. 6) and pulling the adhesive tab toward the proximal end of container 216. The pulling action opens the container along the weakened area 224 to reveal the handle 102 of the catheter 100, which has a gripping surface to facilitate handling. Also, the container can be folded in half to minimize space needed to transport in a purse, bag, or the like.

While the invention has been described in terms of particular variations and illustrative figures, those of ordinary skill in the art will recognize that the invention is not limited to the variations or figures described. Those of ordinary skill in the art will recognize that the invention is not limited to the application of catheters but may be applied to any device that requires similar lubrication. In addition, where methods and steps described above indicate certain events occurring in a certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Further, the features described in one embodiment may generally be combined with features described in other embodiments. Therefore, to the extent there are variations of the invention, which are within the spirit of the disclosure or equivalent to the inventions found in the claims, it is the intent that this patent will cover those variations as well.

What is claimed is:

1. A packaged urinary catheter, comprising:
a urinary catheter including:
 a handle;
 a catheter shaft attached to the handle;
 a base coating over the catheter shaft; and
 an outer coating over the base coating, each coating of the base coating and the outer coating including a combination of components selected from a hydrogel, polyacrylic acid ("PAA"), glycerin, water, and polyethylene glycol ("PEG"); and
a container including the urinary catheter, wherein the container does not include an added moisture source or lubricant for application to the catheter shaft, the base coating and the outer coating in a wet state sufficient for insertion of the catheter shaft into a urethra without the added moisture source or lubricant.

2. The urinary catheter of claim 1, wherein the base coating includes PAA in a range of 0.2 wt % to 3 wt %, glycerin in a range of 15 wt % to 25 wt %, water in a range of 20 wt % to 30 wt %, and PEG 400 in a range of 40 wt % to 60 wt %.

3. The urinary catheter of claim 1, wherein the base coating includes PAA in a range of 0.1 wt % to 2.5 wt %, water in a range of 10 wt % to 45 wt %, and PEG in a range of 20 wt % to 65 wt %.

4. The urinary catheter of claim 1, wherein the hydrogel is glyceryl acrylate/acrylic acid copolymer together with glycerin and propylene glycol.

5. The urinary catheter of claim 4, wherein the outer coating includes hydrogel in a range of 20 wt % to 30 wt %, glycerin in a range of 20 wt % to 30 wt %, and PEG 400 in a range of 40 wt % to 60 wt %.

6. The urinary catheter of claim 4, wherein the outer coating includes hydrogel in a range of 20 wt % to 30 wt %, glycerin in a range of 40 wt % to 60 wt %, and PEG 300 in a range of 20 wt % to 30 wt %.

7. The urinary catheter of claim 4, wherein the outer coating includes hydrogel in a range of 10 wt % to 35 wt %, glycerin in a range of 25 wt % to 75 wt %, PEG 300 in a range of 25 wt % to 65 wt %, and PEG 400 in a range of 25 wt % to 50 wt %.

8. The urinary catheter of claim 4, wherein the outer coating includes hydrogel in a range of 15 wt % to 35 wt %, water in a range of 10 wt % to 45 wt %, and PEG 400 in a range of 20 wt % to 75 wt %.

9. The urinary catheter of claim 4, wherein the outer coating includes hydrogel in a range of 22 wt % to 26 wt %, water at approximately 25 wt %, and PEG 400 is in a range of 49 wt % to 53 wt %.

10. The urinary catheter of claim 1, further comprising:
a silicone film over the outer coating, the silicone film configured to be moved toward the handle of the urinary catheter to expose the outer coating before the insertion of the catheter shaft into the urethra.

11. The urinary catheter of claim 10, wherein the silicone film includes ultraviolet ("UV") light-cured UV agents.

12. The urinary catheter of claim 1, wherein the handle includes a plurality of ridges designed for gripping the handle.

13. The urinary catheter of claim 1, wherein the catheter shaft includes a plurality of eyelets proximate a catheter tip in fluid communication with an opening in a proximal end of the handle by way of a lumen through the urinary catheter.

14. The urinary catheter of claim 13, wherein the plurality of eyelets include two pairs of eyelets circumferentially positioned 90 degrees apart from each other in a non-overlapping configuration.

15. The urinary catheter of claim 1, wherein the container further comprises:
a weakened area of sheet material positioned over at least a portion of the handle of the urinary catheter; and
an adhesive tab covering the weakened area of the sheet material, the adhesive tab including a pull loop configured to open the container about the weakened area of the sheet material when the pull loop is pulled toward an end of the container.

16. A method of manufacturing a packaged urinary catheter, comprising:
folding a sheet material such that longitudinal edges of the sheet material meet;
forming a back seam from the longitudinal edges of the sheet material and, thereby, forming a cavity within the sheet material;
disposing a urinary catheter in the cavity of the sheet material, the urinary catheter including:
 a handle;
 a catheter shaft attached to the handle;
 a base coating over the catheter shaft; and
 an outer coating over the base coating, each coating of the base coating and the outer coating including a combination of components selected from a hydrogel, polyacrylic acid ("PAA"), glycerin, water, and polyethylene glycol ("PEG"); and
sealing ends of the cavity of the sheet material to form a container including the urinary catheter, wherein the container does not include an added moisture source or lubricant for application to the catheter shaft, the base coating and the outer coating in a wet state sufficient for insertion of the catheter shaft into a urethra without the added moisture source or lubricant.

17. The method of claim 16, further comprising:
weakening the sheet material before folding the sheet material, thereby providing a weakened area of the sheet material positioned over at least a portion of the handle of the urinary catheter in the container.

18. The method of claim 17, further comprising:
covering the weakened area of the sheet material with an adhesive tab, the adhesive tab including a pull loop configured to open the container about the weakened area of the sheet material when the pull loop is pulled toward an end of the container.

19. The method of claim 16, wherein the base coating includes either:
i) polyacrylic acid ("PAA") in a range of 0.2 wt % to 3 wt %, glycerin in a range of 15 wt % to 25 wt %, water in a range of 20 wt % to 30 wt %, and polyethylene glycol ("PEG") 400 in a range of 40 wt % to 60 wt %; or
ii) PAA in a range of 0.1 wt % to 2.5 wt %, water in a range of 10 wt % to 45 wt %, and PEG in a range of 20 wt % to 65 wt %.

20. The method of claim 19, wherein the outer coating includes a combination of components selected from a hydrogel, PAA, glycerin, water, and PEG.

\* \* \* \* \*